United States Patent [19]
Lee et al.

[11] Patent Number: 5,175,287
[45] Date of Patent: Dec. 29, 1992

[54] PROCESS FOR PREPARING 1,2,4-BENZOTRIAZINE OXIDES

[75] Inventors: William W. Lee, Palo Alto; J. Martin Brown, Stanford; Edward W. Grange, Palo Alto; Abelardo P. Martinez, San Jose; Michael Tracy, Palo Alto; Daniel J. Pollart, Menlo Park, all of Calif.

[73] Assignee: S R I International, Menlo Park, Calif.

[21] Appl. No.: 409,480

[22] Filed: Sep. 18, 1989

Related U.S. Application Data

[63] Continuation-in-part of Ser. No. 356,602, May 24, 1989, abandoned, which is a continuation of Ser. No. 169,873, Mar. 18, 1988, abandoned, which is a continuation-in-part of Ser. No. 911,906, Sep. 25, 1986, abandoned.

[51] Int. Cl.$^5$ .......................... C07D 253/065
[52] U.S. Cl. .................. 544/183; 544/122; 544/129; 544/142; 544/80
[58] Field of Search .................. 544/80, 112, 183

[56] References Cited

U.S. PATENT DOCUMENTS

| | | | |
|---|---|---|---|
| 2,489,352 | 11/1949 | Wolf et al. | 544/183 |
| 2,489,359 | 11/1949 | Wolf et al. | 544/183 |
| 3,079,390 | 2/1963 | Jiu et al. | 544/183 |
| 3,482,024 | 12/1969 | Molnar et al. | 544/183 |
| 3,868,371 | 2/1975 | Ley et al. | 544/183 |
| 3,957,779 | 5/1976 | Seng et al. | 544/183 |
| 3,980,779 | 9/1976 | Ley et al. | 544/183 |
| 3,991,189 | 11/1976 | Seng et al. | 544/183 |
| 4,001,410 | 1/1977 | Ley et al. | 544/183 |
| 4,027,022 | 5/1977 | Seng et al. | 544/183 |
| 4,067,981 | 1/1978 | Sasse et al. | 544/183 |
| 4,091,098 | 5/1978 | Lumma, Jr. | 544/183 |
| 4,160,833 | 7/1979 | Diel | 544/183 |
| 4,206,212 | 6/1980 | Sasse et al. | 544/183 |
| 4,247,691 | 1/1981 | Diel | 544/183 |
| 4,289,771 | 9/1981 | Sasse et al. | 544/183 |
| 4,316,022 | 2/1982 | Hajos et al. | 544/183 |

FOREIGN PATENT DOCUMENTS

| | | |
|---|---|---|
| 0001090 | 3/1979 | European Pat. Off. . |
| 24043375 | 9/1974 | Fed. Rep. of Germany . |
| 2322140 | 3/1977 | France . |
| 1234845 | 6/1971 | United Kingdom . |
| WO88/02366 | 4/1988 | World Int. Prop. O. . |

OTHER PUBLICATIONS

M. P. Doyle et al., *J. Org. Chem.* 42(22):3494 (1977).
Katritzky et al., *Chemistry of the Heterocyclic N-Oxides*, Blomquist, A. T., Ed.; New York: Academic Press, pp. 216-229 (1971).
Zeman et al., *Int. J. Radiation Oncology Biol. Phys.* 16:977 (1989).
Boyer et al., *J. Org. Chem.* 50:3408 (1985).
Kozuka et al., *Chem. Ind.*:452 (1974).
Kawazoe et al., *Chem. Pharm. Bull.* 13:1103 (1965).
Jui et al., *J. Organ. Chem.* (1959) 24(6):813-818.
Ross et al., *J. Chromatography* (1977) 131:448-452.
Wolf et al., *J. Amer. Chem. Soc.* (1954) 76(13):3551-3553.
Wolf et al., *J. Amer. Chem. Soc.* (1954) 76(18):4611-4613.

(List continued on next page.)

*Primary Examiner*—Robert W. Ramsuer
*Assistant Examiner*—Jacqueline Haley

[57] ABSTRACT

A method of using 1,2,4-benzotriazine oxides, some of which are novel compounds, as radiosensitizers and selective cytotoxic agents is disclosed. These compounds are shown to specifically radiosensitize hypoxic tumor cells. Some are additionally disclosed to be useful as specific cytotoxic agents for these cells. They also show an unexpected ability to radiosensitize aerobic cells following or preceding a hypoxic incubation of the cells with the drug. This provides a basis for selective radiosensitization of tumors compared to normal cells. A novel method for preparing the 1,2,4-benzotriazine oxides is also disclosed.

5 Claims, 5 Drawing Sheets

OTHER PUBLICATIONS

R. H. Atallah et al., *Tetrahedron* 38(12):1793–1796 (1982).

M. A. Baker et al., *Cancer Research* 48:5947–5952 (1988).

K. R. Laderoute et al., *Biochemical Pharmacology* 35(19):3417–3420 (1986; oral presentation given in Oct., 1985).

K. Laderoute et al., *Biochemical Pharmacology* 37(8): 1487–1495 (1988).

J. C. Mason et al., *J. Chem. Soc.* (B) 5:911–916 (1970).

F. Seng et al., *Angew. Chem. Internat. Edit.* 11(11):1009–1010 (1972).

M. I. Walton et al., *J. Chromatogr.* 430(2):429–437 (1988).

E. M. Zeman et al., *Int. J. Radiation Oncology Biol. Phys.* 12:1239–1242 (1986).

E. M. Zeman et al., *Radiotherapy and Oncology* 12:209–218 (1988).

March, J. *Advanced Organic Chemistry,* 3rd edition, p. 646, 1985.

Fieser & Fieser, *Reagents for Organic Synthesis,* vol. 7 Wiley Interscience 1983, pp. 48–49.

FIG. 3  TIME OF INJECTING HYDRALAZINE RELATIVE TO SR 4233 (HOURS)

PROCESS FOR PREPARING 1,2,4-BENZOTRIAZINE OXIDES

REFERENCE TO GOVERNMENT GRANT OR CONTRACT

The invention described herein was made in the course of work under grant or contract from the Department of Health and Human Services. The Government has certain rights in this invention.

This application is a continuation-in-part of U.S. application Ser. No. 356,602, filed May 24, 1989, now abandoned was a continuation of U.S. application Ser. No. 169,873, filed Mar. 18, 1988, now abandoned, which in turn was a continuation-in-part of U.S. application Ser. No. 911,906, filed Sep. 25, 1986, also abandoned.

TECHNICAL FIELD

The invention relates to cytotoxic agents and radiotherapy effective against hydoxic cells. More specifically, the invention relates to certain novel 1,2,4-benzotriazine oxides, to methods of selectively killing tumor cells and/or sensitizing tumor cells to radiation using selected 1,2,4-benzotriazine oxides, and to novel synthetic methods.

BACKGROUND ART

Hypoxic cell radiosensitizers are compounds that selectively increase the sensitivity of hypoxic cells to destructive radiation. Cytotoxins which have enhanced activity under hypoxic conditions also provide a means for selective destruction of cells under low oxygen pressure. This specificity for hypoxic cells is important because it is tumors that are typically characterized by such cells. Virtually all tumors which are present as solid masses contain these cells, while normal cells generally have an adequate supply of oxygen Accordingly, anti-tumor agents can be made selective for tumors by virtue of high activity under hypoxic conditions, and radiation can be employed more effectively in the presence of these sensitizers.

Of course, the use of radiation treatment to destroy tumor cells is only practical if damage to the surrounding normal tissue can be minimized or avoided. The effects of radiation are enhanced by the presence of oxygen, and it is established that as the dose of radiation is increased, the effectiveness of the radiation in destroying target cells is enhanced most dramatically when oxygen is present. Therefore, selectivity for tumor cells toward radiation is difficult to achieve—normal cells, in view of their oxygen supply, are generally more susceptible to radiation than the target tumor cells. It is therefore desirable to provide a means of sensitizing tumor cells, but not the surrounding tissue, to radiation treatment. One solution would be to increase the supply of oxygen to these tumor cells. This, however, has proved difficult to do.

Various heterocyclic compounds and in particular those with oxidized nitrogen moieties, have been used to radiosensitize hypoxic tumor cells. Indeed, it has been postulated that the oxidized nitrogen functionality is responsible for this activity. Nitroimidazoles, particularly misonidazole (MIS) and metronidazole have been studied extensively, and MIS is commonly used as a standard in in vitro and in vivo tests for radiosensitizing activity. (See, e.g., Asquith, et al, *Radiation Res* (1974) 60:108-118; Hall, et al, *Brit J Cancer* (1978) 37: 567-569; Brown, et al. *Radiation Res* (1980) 82:171-190; and U.S. Pat. No. 4,371,540. The radiosensitizing activities of certain 1-substituted 3(5)-nitro-s-triazoles and, of various quinoxaline-1,4-dioxide derivatives have also been disclosed.

In addition, U.S. Ser. Nos. 730,761, filed May 3, 1985, now abandoned and 788,762, filed Oct. 18, 1985 assigned to the same assignee and incorporated by reference disclose a group of radiosensitizers that do not contain oxidized nitrogen—the substituted benzamides and nicotinamides and their thio analogs. These compounds, nevertheless, are radiosensitizers. It is important to distinguish the ability to sensitize hypoxic cells selectively, for instance, by enhancing their oxygen supply, from another mechanism commonly encountered for "sensitizing" cells: inhibition of the enzyme poly(ADP-ribose)polymerase, which is believed to be essential in the repair of irradiated cells after radiation. This repair mechanism is operative in both hypoxic tumor cells and in normal cells. Hence, administration of "radiosensitizers" which operate according to this latter mechanism does not accomplish the desired purpose of selectively sensitizing the target tumor cells.

A group of compounds which has not previously been suggested for use in either selectively killing hypoxic cells or in radiosensitizing such cells is 3-amino-1,2,4-benzotriazine 1,4-di-N-oxide and related compounds. Related U.S. Pat. Nos. 3,980,779; 3,868,371; and 4,001,410 disclose the preparation of a group of these compounds and their use as anti-microbial agents, particularly by addition of these materials to livestock fodder. U.S. Pat. Nos. 3,991,189 and 3,957,799 disclose derivatives of these compounds bearing substituents on the nitrogen of the 3-amino group. These compounds also have anti-microbial activity.

The present invention provides additional compounds which specifically radiosensitize hypoxic cells and which, furthermore, are directly cytotoxic to hypoxic cells both in vitro and in vivo. Therefore, administration of these compounds prior to or following radiation treatment of tumors selectively kills the hypoxic (tumor) cells which survive the radiation dose. Both the ability of these compounds to radiosensitize hypoxic cells and especially their ability to selectively kill hypoxic cells directly are unexpected properties of these compounds.

The invention also provides novel 1,2,4-benzotriazine oxides useful as radiosensitizers and/or selective cytotoxic agents; methods of synthesizing the compounds; and methods of administering the compounds to achieve radiosensitization and/or selective cell killing.

Disclosure of the Invention

The invention provides a valuable addition to the group of compounds currently available as selective radiosensitizers and selective cytotoxic agents for hypoxic tumor cells. Some of the compounds now newly shown to be useful in this regard are known compounds. Others are themselves novel.

Accordingly, one aspect of the invention is a method of radiosensitizing hypoxic tumor cells by administering to these cells a compound of the formula:

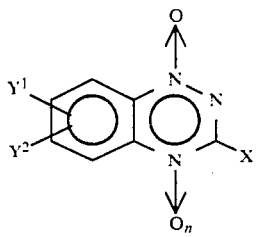

wherein X is H; hydrocarbyl (1-4C); hydrocarbyl (1-4C) substituted with OH, NH₂, NHR or NRR; halogen; OH; alkoxy (1-4C); NH₂; NHR or NRR; wherein the various R groups are independently selected from lower alkyl (1-4C) and lower acyl (1-4C) and the R's may themselves be substituted with OH, NH₂, alkyl (1-4C) secondary and dialkyl (1-4C) tertiary amino groups, alkoxy (1-4C) or halogen. In the case of NRR, the two R's can be linked together directly or through a bridge oxygen into a morpholino ring, pyrrolidino ring or piperidino ring;

n is 0 or 1; and $Y^1$ and $Y^2$ are independently either H; nitro; halogen; hydrocarbyl (1-14C) including cyclic and unsaturated hydrocarbyl, optionally substituted with 1 or 2 substituents selected from the group consisting of halogen, hydroxy, epoxy, alkoxy (1-4C), alkylthio (1-4C), primary amino (NH₂), alkyl (1-4C) secondary amino, dialkyl (1-4C) tertiary amino, dialkyl (1-4C) tertiary amino where the two alkyls are linked together to produce a morpholino, pyrrolidino or piperidino, acyloxy (1-4C), acylamido (1-4C) and thio analogs thereof, acetylaminoalkyl (1-4C), carboxy, alkoxycarbonyl (1-4C), carbamyl, alkylcarbamyl (1-4C), alkylsulfonyl (1-4C) or alkylphosphonyl (1-4C), wherein the hydrocarbyl can optionally be interrupted by a single ether (—O—) linkage; or wherein $Y^1$ and $Y^2$ are independently either morpholino, pyrrolidino, piperidino, NH₂, NHR', NR'R' O (CO)R', NH(CO)R', O(SO)R', or O (POR')R' in which R' is a hydrocarbyl (1-4C) which may be substituted with OH, NH₂,alkyl (1-4C) secondary amino, dialkyl (1-4C) tertiary amino, morpholino, pyrrolidino, piperidino, alkoxy (1-4C), or halogen substituents, or pharmacologically acceptable salts of said compound.

In another aspect, the invention provides an improved method of fractionated radiotherapy which involves treating the cells requiring radiotherapy with a 1,2,4-benzotriazine oxide of Formula (I), as just defined, before or after subjecting the treated cells to a plurality of distinct radiation doses over an extended period of time, each of the radiation doses being less than about 5 Gy.

The compounds useful in conjunction with the presently disclosed radiosensitizing methods, therefore, are the mono- or dioxides of optionally substituted 1,2,4-benzotriazine which may contain a hydrocarbyl (1-4C), hydroxyl, alkoxy or amino group, either substituted or unsubstituted, in the 3-position, and their pharmacologically acceptable salts as set forth in Formula I The invention also provides a method for selectively killing hypoxic tumor cells using certain of these 1,2,4-benzotriazine oxides. The compounds which are useful as selective cytotoxic agents are a subset of the above-defined compounds useful as radiosensitizers. That is, while all of the compounds defined by Formula (I) are generally effective as radiosensitizers, only those compounds unsubstituted at the 3-position or having a 3-amino or 3-hydrocarbyl (1-4C) substituent (i.e., X = H, hydrocarbyl (1-4C), NH₂, NHR or NRR with each R as defined above) and which are di-N-oxides (n = 1) are effective cytotoxic agents. In this aspect, the invention provides a method of selectively killing hypoxic tumor cells by administering one or more of these compounds (or its salts) to the hypoxic tumor cells.

Certain of the compounds encompassed by Formula (I) are already known in the art as being useful for other purposes; other compounds are novel. The novel compounds encompassed by the present invention and which may be prepared by methods disclosed herein include compounds represented by Formula (I), in which the substituents fall into the following three classes:

I. X is OH, alkoxy (1-4C), NHR or NRR where each R is independently an alkyl of 1-4 carbon atoms, or acyl of 1-4 carbon atoms, or where the two R groups are alkyls linked together to form a pyrrolidino or piperidino ring or linked through an oxygen to form a morpholino ring, and the R groups may be further substituted with OH, NH ₂, alkyl (1-4C) secondary amino, dialkyl (1-4C) tertiary amino, pyrrolidino, piperidino, alkoxy (1-4C), or halogen substitutents;

n is 1; and $Y^1$ and $Y^2$ are independently either H; nitro; halogen; hydrocarbyl (1-14C) including cyclic and unsaturated hydrocarbyl, optionally substituted with 1 or 2 substituents selected from the group consisting of halogen, hydroxy, epoxy, alkoxy (1-4C), alkylthio (1-4C), primary amino (NH₂), alkyl (1-4C) secondary amino, dialkyl (1-4C) tertiary amino, dialkyl tertiary amino where the two alkyls are linked together to produce a morpholino, pyrrolidino or piperidino, acyloxy (1-4C), acylamido (1-4C) and thio analogs thereof, acetylaminoalkyl (1-4C), carboxy, alkoxycarbonyl (1-4C), carbamyl, alkylcarbamyl (1-4C), alkylsulfonyl (1-4C) or alkylphosphonyl (1-4C), wherein the hydrocarbyl can optionally be interrupted by a single ether (—O—) linkage; or wherein $Y^1$ and $Y^2$ are independently either morpholino, pyrrolidino, piperidino, NH ₂, NHR', NR'R' (CO)R', NH(CO)R', O (SO)R', or O (POR')R' in which R' is a hydrocarbyl (1-4C) which may be substituted with OH, NH ₂, alkyl (1-4C) secondary amino, dialkyl (1-4C) tertiary amino, morpholino, pyrrolidino, piperidino, alkoxy (1-4C), or halogen substitutents. Pharmacologically acceptable salts of these compounds are also included in this class of compounds.

II X is NH₂;

n is 1; and $Y^1$ and $Y^2$ are chosen such that one but not both may be hydrogen and one or both may independently be either nitro, saturated or unsaturated hydrocarbyl of 7-14C, or unsaturated hydrocarbyl of 2-6C, optionally substituted with 1 or 2 substituents selected from the group consisting of halogen, hydroxy, epoxy, alkoxy (1-4C) alkylthio (1-4C), primary amino (NH₂), alkyl (1-4C) secondary amino, dialkyl (1-4C) tertiary amino, dialkyl tertiary amino where the two alkyls are linked together to produce a morpholino, pyrrolidino or piperidino, acyloxy (1-4C), acylamido (1-4) and thio analogs thereof, acetylaminoalkyl (1-4C), carboxy, alkoxycarbonyl (1-4C), carbamyl, alkylcarbamyl (1-4C), alkylsulfonyl (1-4C) and alkylphosphonyl (1-4C), wherein the hydrocarbyl can optionally be interrupted by a single ether (—O—) linkage; or wherein $Y^1$ and $Y^2$ are independently either morpholino, pyrrolidino, piperidino, NH$_2$, NHR', NR'R' O (CO)R', NH(CO)R', O (SO)R', or O (POR')R' in which R' is a hydrocarbyl (1-4C) which may be substituted with OH, NH$_2$, alkyl (1-4C) secondary amino, dialkyl (1-4C) tertiary amino, morpholino, pyrrolidino, piperidino, alkoxy (1-4C), or halogen substituents. Pharmacologically acceptable salts of these compounds are also included in this class of compounds.

III. X is hydrogen or hydrocarbyl (2-4C) optionally substituted with OH, NH$_2$, alkoxy (1-4C) or halogen substituents;

n is 1; and

Y$^1$ and Y$^2$ are independently either H; nitro; halogen; hydrocarbyl (1-14C) including cyclic and unsaturated hydrocarbyl, optionally substituted with 1 or 2 substituents selected from the group consisting of halogen, hydroxy, epoxy, alkoxy (1-4C), alkylthio (1-4C), primary amino (NH$_2$), alkyl (1-4C) secondary amino, dialkyl (1-4C) tertiary amino, dialkyl tertiary amino where the two alkyls are linked together to produce a morpholino, pyrrolidino or piperidino, acyloxy (1-4C), acylamido (1-4C) and thio analogs thereof, acetylaminoalkyl (1-4C), carboxy, alkoxycarbonyl (1-4C), carbamyl, alkylcarbamyl (1-4C), alkylsulfonyl (1-4C) or alkylphosphonyl (1-4C), wherein the hydrocarbyl can optionally be interrupted by a single ether (—O—) linkage; or wherein Y$^1$ and Y$^2$ are independently either morpholino, pyrrolidino, piperidino, NH$_2$, NHR', NR'R' O (CO)R', NH(CO)R', O (SO)R', or O (POR')R' in which R' is a hydrocarbyl (1-4C) which may be substituted with OH, NH$_2$, alkyl (1-4C) secondary amino, dialkyl (1-4C) tertiary amino, morpholino, pyrrolidino, piperidino, alkoxy (1-4C), or halogen substituents. Pharmacologically acceptable salts of these compounds are also included in this class of compounds.

The invention also provides a straightforward, one-step synthesis for preparing 1,2,4-benzotriazine oxides unsubstituted at the 3-position (i.e., the compounds of Formula (I) wherein X=H) by treating the corresponding 3-amino-1,2,4-benzotriazine oxide with a lower alkyl nitrite under reductive deaminating conditions.

MODES OF CARRYING OUT THE INVENTION

Figure 1:
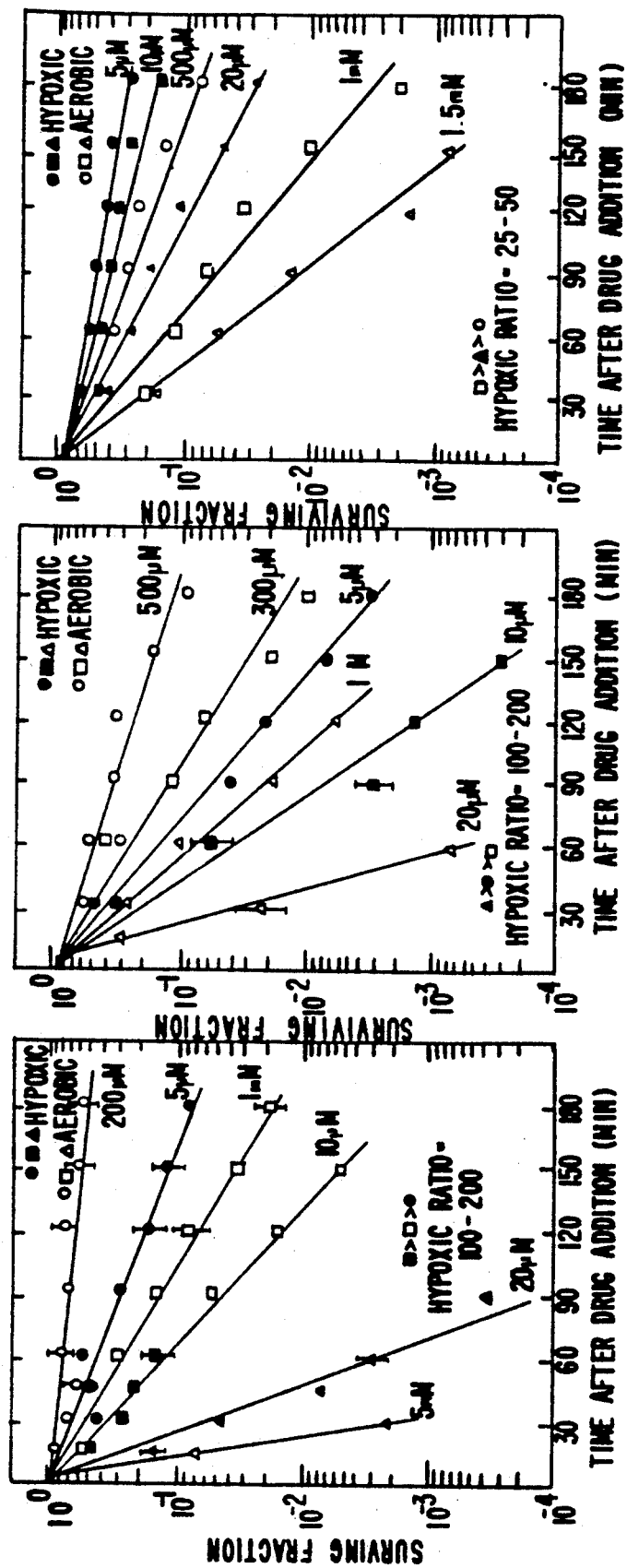
FIGS. 1A, 1B and 1C show the selective cytotoxicity of 3-amino-1,2,4-benzotriazine 1,4-dioxide for hypoxic cells derived from hamster, mouse and human tissues.

A. The Compounds Useful in the Invention

The compounds useful as radiosensitizers and selective cytotoxic agents as described herein are derivatives of 1,2,4-benzotriazine oxide represented by Formula (I).

These compounds, as shown in the Formula (I), contain a group X in their 3 position. X will vary specifically as set forth above, depending upon the activity desired. Subject to the above-recited selection criteria, X is chosen in general from hydrogen; unsubstituted hydrocarbyls (1-4C) such as methyl, ethyl, s-butyl and the like; hydroxy; alkoxy (1-4C) such as methoxy, ethoxy, propoxy, t-butoxy and the like; primary amino (NH$_2$); secondary amino (NHR) where R is an alkyl or acyl of 1 to 4 carbons, such as methylamino, ethylamino and the like; tertiary amino (NRR) where each of the R groups is an alkyl or acyl of 1 to 4 carbons, for example diethylamino and the like, or the two R's join to form a morpholino, pyrrolidino or piperidino ring. In the case of the various alkyl and acyl R groups, they can be further substituted with OH, NH$_2$, lower alkyl (1-4C) secondary amino and dialkyl (1-4C) tertiary amino, morpholino pyrrolidino, piperidino, alkoxy (1-4C) or halogen (fluoro, chloro, bromo or iodo) substituents.

In the case of the hydrocarbyl X groups, they can be further substituted with OH, NH$_2$, alkyl secondary amino, dialkyl tertiary amino, alkoxy (1-4C) or halogen (fluoro, chloro, bromo or iodo) substituents.

The compounds of Formula (I) additionally contain groups Y$^1$ and Y$^2$. These groups are selected specifically according to the criteria set forth above, depending upon the utility desired.

Subject to these criteria, Y$^1$ and Y$^2$ may be selected from hydrogen; nitro; halogen (e.g. fluoro, chloro, bromo or iodo); or hydrocarbyl (1-14C). When hydrocarbyl, Y$^1$ or Y$^2$ may be saturated or unsaturated, cyclic or acyclic, and may optionally be interrupted by a single ether linkage. Thus, the unsubstituted hydrocarbyl forms of Y$^1$ or Y$^2$ can be, for example, methyl, ethyl, n-propyl, s-butyl, n-hexyl, 2-methyl-n-pentyl, 2-ethoxyethyl, 3-(n-propoxy)-n-propyl, 4-methoxybutyl, cyclohexyl, tetrahydrofurfuryl, furfuryl, cyclohexenyl, 3-(n-decyloxy)-n-propyl, 4-methyloctyl, 4,7-dimethyloctyl, or the like.

The hydrocarbyl Y$^1$ and Y$^2$ groups may optionally be substituted with 1 or 2 substituents selected from halogen such as fluoro, chloro, bromo or iodo; hydroxy; epoxy; alkoxy (1-4C) such as, for example, methoxy, n-propoxy and t-butoxy; alkyl thio; (1-4C) primary amino (NH$_2$); morpholino; pyrrolidino; piperidino; secondary amino (NHR') where R' is a 1-4C alkyl, such as methylamino, propylamino and the like; tertiary amino (NR'R'); acyloxy and acylamido groups represented by R'COO— and R'CONH—, respectively, and their thiol analogs represented by R'CSO—and R'CSNH—respectively; carboxy (—C(O)OH); alkoxycarbonyl (—C(O)OR' ; carbamyl (—C(O)NH$_2$); alkylcarbamyl (1-4C) (—C(O)NHR'); alkylsulfonyl (1-4C) (R'SO$_2$—); and alkyl phosphonyl (1-4C) ( R'P(OR')O—).

In addition Y$^1$ and Y$^2$ can each independently be —NH$_2$, —NHR', —NR'R', —OCOR', —NH(CO)R', O (SO)R' or —O(POR')R' in which the various R' groups are lower alkyls (1-4C) which themselves may be substituted with OH, NH$_2$, alkyl secondary and tertiary amino, pyrrolidino, piperidino, alkoxy (1-4C), or halogen substitutents.

A particularly promising class of compounds for use both as radiosensitizers and selective cytotoxic agents include those represented by the following structural Formula (II):

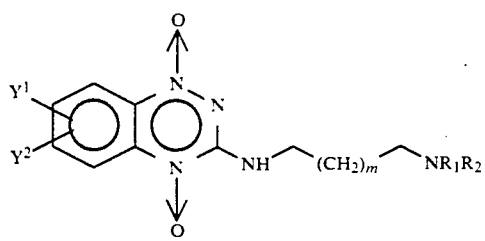

In Formula (II), one of $Y^1$ and $Y^2$ is H, the other an electron-withdrawing group (e.g., nitro, carboxy, alkoxycarbonyl, alkylsulfonyl), $R_1$ and $R_2$ are independently selected from the group consisting of hydrogen and lower alkyl, or the $R_1$ and $R_2$ groups may be linked to form a piperidino or pyrrolidino ring, and m is an integer from 0-4 inclusive, preferably 1 or 2.

Where X is OH, of course, the compounds may also be prepared and used as the pharmaceutically acceptable salts formed from inorganic gases, such as sodium, potassium, or calcium hydroxide, or from organic bases, such as caffeine, ethylamine, and lysine.

When X is $NH_2$, NHR, or NRR, e.g., $NH-CH_2-(CH_2)_m-CH_2NR_1R_2$ as in Formula (II), pharmaceutically acceptable acid addition salts may be used. These salts are those with inorganic acids such as hydrochloric, hydrobromic or phosphoric acids or organic acids such as acetic acid, pyruvic acid, succinic acid, mandelic acid, p-toluene sulfonic acid, and so forth. (Amino substituents on the hydrocarbyl side chain can also, of course, be converted to salts.)

The 1,2,4-benzotriazines may be used in the practice of this invention as the mono- or dioxides; i.e. either the 1-nitrogen of the triazino ring may be oxidized, or both the 1-and 4-nitrogens may be oxidized.

Specific particularly preferred compounds which are useful in the radiosensitization and cytotoxic procedures of the invention include
3-hydroxy-1,2,4-benzotriazine 1-oxide;
3-hydroxy-1,2,4-benzotriazine 1,4-dioxide;
3-amino-1,2,4-benzotriazine 1-oxide;
3-amino-1,2,4-benzotriazine 1,4-di-oxide;
6(7)-methoxy-3-hydroxy-1,2,4-benzotriazine 1-oxide;
6(7)-methoxy-3-hydroxy-1,2,4-benzotriazine 1,4-dioxide;
6(7)-methoxy-3-amino-1,2,4-benzotriazine 1-oxide;
6(7)-methoxy-3-amino-1,2,4-benzotriazine 1,4-dioxide;
6(7)-ethoxy-3-hydroxy-1,2,4-benzotriazine 1-oxide;
6(7)-ethoxy-3-hydroxy-1,2,4-benzotriazine 1,4-dioxide;
6(7)-ethoxy-3-amino-1,2,4-benzotriazine 1-oxide;
6(7)-ethoxy-3-amino-1,2,4-benzotriazine 1,4-dioxide;
6(7)-[4-acetamido-n-butanoxy]-3-hydroxy-1,2,4-benzotriazine 1-oxide;
6(7)-[4-acetamido-n-butanoxy]-3-hydroxy-1,2,4-benzotriazine 1,4-dioxide;
6(7)-[4-acetatamido-n-butanoxy]-3-amino-1,2,4-benzotriazine 1-oxide;
6(7)-[4-acetatamido-n-butanoxy]-3-amino-1,2,4-benzotriazine 1,4-dioxide;
6(7)-[1-(2,3-dihydroxy)propoxy]-3-hydroxy-1,2,4-benzotriazine 1-oxide;
6(7)-[1-(2,3-dihydroxy)propoxy]-3-hydroxy-1,2,4-benzotriazine 1,4-dioxide;
6(7)-[1-(2,3-dihydroxy)propoxy]-3-amino-1,2,4-benzotriazine 1-oxide;
6(7)-[1-(2,3-dihydroxy)propoxy]-3-amino-1,2,4-benzotriazine 1,4-dioxide;
6(7)-[(2-furyl)methylamino]-3-hydroxy-1,2,4-benzotriazine 1-oxide;
6(7)-[(2-furyl)methylamino]-3-hydroxy-1,2,4-benzotriazine 1,4-dioxide;
6(7)-[(2-furyl)methylamino]-3-amino-1,2,4-benzotriazine 1-oxide;
6(7)-[(2-furyl)methylamino]-3-amino-1,2,4-benzotriazine 1,4-dioxide;
6(7)-(2-methoxyethylamino)-3-hydroxy-1,2,4-benzotriazine 1-oxide;
6(7)-(2-methoxyethylamino)-3-hydroxy-1,2,4-benzotriazine 1,4-dioxide;
6(7)-(2-methoxyethylamino)-3-amino-1,2,4-benzotriazine 1-oxide;
6(7)-(2-methoxyethylamino)-3-amino-1,2,4-benzotriazine 1,4-dioxide;
6(7)-carbethoxymethoxy-3-hydroxy-1,2,4-benzotriazine 1-oxide;
6(7)-carbethoxymethoxy-3-hydroxy-1,2,4-benzotriazine 1,4-dioxide;
6(7)-carbethoxymethoxy-3-amino-1,2,4-benzotriazine 1-oxide;
6(7)-carbethoxymethoxy-3-amino-1,2,4-benzotriazine 1,4-dioxide;
6(7)-[(2-methoxyethyl)carbamylmethoxy]-3-hydroxy-1,2,4-benzotriazine 1-oxide;
6(7)-[(2-methoxybamylmethoxy]-3-hydroxy-1,2,4-benzotriazine 1,4-dioxide;
b(7)-[(2-methoxyethyl)carbamylmethoxy]-3-amino-1,2,4-benzotriazine 1-oxide;
6(7)-[(2-methoxyethyl)carbamylmethoxy]-3-amino-1,2,4-benzotriazine 1,4-dioxide;
6(7)-[(2-hydroxyethyl)carbamylmethoxy]-3-hydroxy-1,2,4-benzotriazine 1-oxide;
6(7)-[(2-hydroxyethyl)carbamylmethoxy]-3-hydroxy-1,2,4-benzotriazine 1,4-dioxide;
6(7)-[(2-hydroxyethyl)carbamylmethoxy]-3-amino-1,2,4-benzotriazine 1-oxide;
6(7)-[(2-hydroxyethyl)carbamylmethoxy]-3-amino-1,2,4-benzotriazine 1,4-dioxide;
6(7)-[1-(2-hydroxy-3-morpholino)propoxy]-3-hydroxy-1,2,4-benzotriazine 1-oxide;
6(7)-[1-(2-hydroxy-3-morpholino)propoxy]-3-hydroxy-1,2,4-benzotriazine 1,4-dioxide:
6(7)-[1-(2-hydroxy-3-morpholino)propoxy]-3-amino-1,2,4 benzotriazine 1-oxide;
6(7)-11-(2-hydroxy-3-morpholino)propoxy]-3-amino-1,2,4 benzotriazine 1,4-dioxide;
6(7)-[3-amino-n-propoxy]-3-hydroxy-1,2,4-benzotriazine 1-oxide;
6(7)-[3-amino-n-propoxy]-3-hydroxy-1,2,4-benzotriazine 1,4-dioxide;
6(7)-[3-amino-n-propoxy]-3-amino-1,2,4-benzotriazine 1-oxide;
6(7)-[3-amino-n-propoxy]-3-amino-1,2,4-benzotriazine 1,4-dioxide;
6(7)-[2,3-epoxypropoxy]-3-hydroxy-1,2,4-benzotriazine 1-oxide;
6(7)-[2,3-epoxypropoxy]-3-hydroxy-1,2,4-benzotriazine 1,4-dioxide;
6(7)-[2,3-epoxypropoxy]-3-amino-1,2,4-benzotriazine 1-oxide;

6(7)-[2,3-epoxypropoxy]-3-amino-1,2,4-benzotriazine 1,4-dioxide;
6(7)-[3-methoxy-2-hydroxy-n-propoxy]-3-hydroxy-1,2,4-benzotriazine 1-oxide;
6(7)-[3-methoxy-2-hydroxy-n-propoxy]-3-hydroxy-1,2,4-benzotriazine 1,4-dioxide;
6(7)-13-methoxy-2-hydroxy-n-propoxy]-3-amino-1,2,4-benzotriazine 1-oxide;
6(7)-[3-methoxy-2-hydroxy-n-propoxy]-3-amino-1,2,4-benzotriazine 1,4-dioxide;
6(7)-14-ethoxy-3-hydroxy-n-butoxy]-3-hydroxy-1,2,4-benzotriazine 1-oxide;
6(7)-[4-ethoxy-3-hydroxy-n-butoxy]-3-hydroxy-1,2,4-benzotriazine 1,4-dioxide;
6(7)-[4-ethoxy-3-hydroxy-n-butoxy]-3-amino-1,2,4-benzotriazine 1-oxide;
6(7)-[4-ethoxy-3-hydroxy-n-butoxy]-3-amino-1,2,4-benzotriazine 1,4-dioxide;
6(7)-[3,4-dihydroxy-n-butoxy]-3-hydroxy-1,2,4-benzotriazine 1-oxide;
6(7)-[3,4-dihydroxy-n-butoxy]-3-hydroxy-1,2,4-benzotriazine 1,4-dioxide;
6(7)-[3,4-dihydroxy-n-butoxy]-3-amino-1,2,4-benzotriazine 1-oxide;
6(7)-13,4-dihydroxy-n-butoxy]-3-amino-1,2,4-benzotriazine 1,4-dioxide;
6(7)-methyl-3-hydroxy-1,2,4-benzotriazine 1-oxide;
6(7)-methyl-3-hydroxy-1,2,4-benzotriazine 1,4-dioxide;
6(7)-methyl-3-amino-1,2,4-benzotriazine 1-oxide;
6(7)-methyl-3-amino-1,2,4-benzotriazine 1,4-dioxide;
6(7)-ethyl-3-hydroxy-1,2,4-benzotriazine 1-oxide;
6(7)-ethyl-3-hydroxy-1,2,4-benzotriazine 1,4-dioxide;
6(7)-ethyl-3-amino-1,2,4-benzotriazine 1-oxide;
6(7)-ethyl-3-amino-1,2,4-benzotriazine 1,4-dioxide;
6(7)-chloroacetamido-3-hydroxy-1,2,4-benzotriazine 1-oxide;
6(7)-chloroacetamido-3-hydroxy-1,2,4-benzotriazine 1,4-dioxide;
6(7)-chloroacetamido-3-amino-1,2,4-benzotriazine 1-oxide;
6(7)-chloroacetamido-3-amino-1,2,4-benzotriazine 1,4-dioxide;
6(7)-[(2-hydroxyethyloxy)acetamido]-3-hydroxy-1,2,4-benzotriazine 1-oxide;
6(7)-[(2-hydroxyethyloxy)acetamido]-3-hydroxy-1,2,4-benzotriazine 1,4-dioxide;
6(7)-[(2-hydroxyethyloxy)acetamido]-3-amino-1,2,4-benzotriazine 1-oxide;
6(7)-[(2-hydroxyethyloxy)acetamido]-3-amino-1,2,4-benzotriazine 1,4-dioxide;
6,7-dimethoxy-3-hydroxy-1,2,4-benzotriazine 1-oxide;
6,7-dimethoxy-3-hydroxy-1,2,4-benzotriazine 1,4-dioxide;
6,7-dimethoxy-3-amino-1,2,4-benzotriazine 1-oxide;
6,7-dimethoxy-3-amino-1,2,4-benzotriazine 1,4-dioxide;
6,7-diethoxy-3-hydroxy-1,2,4-benzotriazine 1-oxide;
6,7-diethoxy-3-hydroxy-1,2,4-benzotriazine 1,4-dioxide;
6,7-diethoxy-3-amino-1,2,4-benzotriazine 1-oxide;
6,7-diethoxy-3-amino-1,2,4-benzotriazine 1,4-dioxide;
6(7)-propionyl-3-hydroxy-1,2,4-benzotriazine 1-oxide;
6(7)-propionyl-3-hydroxy-1,2,4-benzotriazine 1,4-dioxide;
6(7)-propionyl-3-amino-1,2,4-benzotriazine 1-oxide;
6(7)-propionyl-3-amino-1,2,4-benzotriazine 1,4-dioxide;
6(7)-(2-acetoxyethoxy)-3-hydroxy-1,2,4-benzotriazine 1-oxide;
6(7)-(2-acetoxyethoxy)-3-hydroxy-1,2,4-benzotriazine 1,4-dioxide;
6(7)-(2-acetoxyethoxy)-3-amino-1,2,4-benzotriazine 1-oxide;
6(7)-(2-acetoxyethoxy)-3-amino-1,2,4-benzotriazine 1,4-dioxide;
6(7)-n-hexyloxy-3-hydroxy-1,2,4-benzotriazine 1-oxide;
6(7)-n-hexyloxy-3-amino-1,2,4-benzotriazine 1,4-dioxide;
6(7)-n-hexyloxy-3-amino-1,2,4-benzotriazine 1-oxide;
6(7)-n-hexyloxy-3-amino-1,2,4-benzotriazine 1,4-dioxide;
6(7)-ethylamino-3-hydroxy-1,2,4-benzotriazine 1-oxide;
6(7)-ethylamino-3-hydroxy-1,2,4-benzotriazine 1,4-dioxide;
6(7)-ethylamino-3-amino-1,2,4-benzotriazine 1-oxide;
6(7)-ethylamino-3-amino-1,2,4-benzotriazine 1,4-dioxide;
6(7)-(2-methoxyethoxy)-3-hydroxy-1,2,4-benzotriazine 1-oxide;
6(7)-(2-methoxyethoxy)-3-hydroxy-1,2,4-benzotriazine 1,4-dioxide;
6(7)-(2-methoxyethoxy)-3-amino-1,2,4-benzotriazine 1-oxide;
6(7)-(2-methoxyethoxy)-3-amino-1,2,4-benzotriazine 1,4-dioxide;
6(7)-(aminoacetamido)-3-hydroxy-1,2,4-benzotriazine 1-oxide;
6(7)-(aminoacetamido)-3-hydroxy-1,2,4-benzotriazine 1,4-dioxide;
6(7)-(aminoacetamido)-3-amino-1,2,4-benzotriazine 1-oxide;
6(7)-(aminoacetamido)-3-amino-1,2,4-benzotriazine 1,4-dioxide;
6(7)-(carbamylmethoxy)-3-hydroxy-1,2,4-benzotriazine 1-oxide;
6(7)-(carbamylmethoxy)-3-hydroxy-1,2,4-benzotriazine 1,4-dioxide;
6(7)-(carbamylmethoxy)-3-amino-1,2,4-benzotriazine 1-oxide;
6(7)-(carbamylmethoxy)-3-amino-1,2,4-benzotriazine 1,4-dioxide;
6(7)-(carboxymethoxy)-3-hydroxy-1,2,4-benzotriazine 1-oxide;
6(7)-(carboxymethoxy)-3-hydroxy-1,2,4-benzotriazine 1,4-dioxide;
6(7)-(carboxymethoxy)-3-amino-1,2,4-benzotriazine 1-oxide;
6(7)-(carboxymethoxy)-3-amino-1,2,4-benzotriazine 1,4-dioxide;
6(7)-[1,2-dihydroxyethyl]-3-amino-1,2,4-benzotriazine 1,4-dioxide;
6(7)-[1-(3-ethylamino-2-hydroxypropoxy)[-3-amino-1,2,4-benzotriazine 1,4-dioxide;
6(7)-[2-ethylamino-1-hydroxyethyl]-3-amino-1,2,4-benzotriazine 1,4-dioxide;
6(7)-[2-hydroxyethyl]-3-amino-1,2,4-benzotriazine 1,4-dioxide;
6(7)-[1-hydroxyethyl]-3-amino-1,2,4-benzotriazine 1,4-dioxide;
3-(2-hydroxyethylamino)-1,2,4-benzotriazine 1-oxide;
3-(2-hydroxyethylamino)-1,2,4-benzotriazine 1,4-dioxide;
6(7)-chloro-3-(2-hydroxyethylamino)-1,2,4-benzotriazine 1-oxide;
6(7)-chloro-3-(2-hydroxyethylamino)-1,2,4-benzotriazine 1,4-dioxide; 3-(1-hydroxyethylamino)-1,2,4-benzotriazine 1-oxide;
3-(1-hydroxyethylamino)-1,2,4-benzotriazine 1,4-dioxide;

1,2,4-benzotriazine 1-oxide;
1,2,4-benzotriazine 1,4-dioxide;
3-methyl-1,2,4-benzotriazine 1,4-dioxide;
3-ethyl-1,2,4-benzotriazine 1,4-dioxide;
3-propyl-1,2,4-benzotriazine 1,4-dioxide;
6(7)-amino-1,2,4-benzotriazine 1,4-dioxide;
6(7)-amino-3-methyl-1,2,4-benzotriazine 1,4-dioxide;
6(7)-amino-3-ethyl-1,2,4-benzotriazine 1,4-dioxide;
6(7)-methoxy-1,2,4-benzotriazine 1,4-dioxide;
6(7)-methoxy-3-methyl-1,2,4-benzotriazine 1,4-dioxide;
6(7)-[1-(2,3-dihydroxypropoxy]-1,2,4-benzotriazine 1,4-dioxide;
6(7)-[1,2-dihydroxyethyl]-1,2,4-benzotriazine 1,4-dioxide;
6(7)-[1-(3-ethylamino-2-hydroxypropoxy)]-1,2,4-benzotriazine 1,4-dioxide;
6(7)-[2-ethylamino-1-hydroxyethyl]-1,2,4-benzotriazine 1,4-dioxide;
6(7)-chloro-1,2,4-benzotriazine 1,4-dioxide;
6(7)-[2-hydroxyethyl]-1,2,4-benzotriazine 1,4-dioxide;
6(7)-[1-hydroxyethyl]-1,2,4-benzotriazine 1,4-dioxide;
6(7)-nitro-3-amino-1,2,4-benzotriazine 1,4-dioxide;
3-(3-N,N-diethylaminopropylamino)-1,2,4-benzotriazine 1,4-dioxide;
6(7)-nitro-3-(2-N,N-diethylaminoethylamino)-1,2,4-benzotriazine 1,4-dioxide;
and their pharmaceutically acceptable salts and the thioamide analogs of the foregoing list of compounds. It should be noted that the $Y^1$ and $Y^2$ substituents set forth in most of the above compounds as present in either the 6 or 7 positions (designated "6(7)") or in both the 6 and 7 positions (designated "6,7") may also be present at the 5 and/or 8 ring positions.

B. Preparation of the Compounds of the Invention

General methods for preparing some 3-amino derivatives are found in the above-referenced patents to Ley et al., for example U.S. Pat. No. 3,980,779. The compounds are prepared from benzofuroxan of the formula:

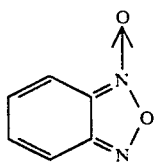

by reaction with a salt of cyanamide, followed by acidification of the reaction mixture. The benzofuroxan starting material is not symmetric with respect to its own 5 and 6 positions (which are the 6 and 7 positions of the resulting 3-amino benzotriazine oxide). Therefore, a mixture of the 6- and 7-substituted materials may result. If desired, this mixture can be separated using conventional means into individual components having a substituent in either the 6 or 7 position.

The dioxide may also be prepared from the parent monoxide or 1,2,4-benzotriazine by peracid oxidation (see Robbins et al, *J Chem Soc* 3186 (1957) and Mason et al, *J Chem Soc B* 911 (1970)).

In addition, the monoxide may be prepared by:
(1) cyclization of a 1-nitro-2-aminobenzene compound using $H_2NCN \cdot 2HCl$;
(2) oxidation of the parent compound given by the structure

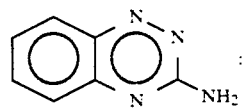

or by controlled reduction of the corresponding dioxide (see Mason, supra, and Wolf et al, *J Am Chem Soc* 76:355 (1954)).

The 1,2,4-benzotriazines may be prepared by cyclization of formazan precursors using $BF_3/AcOH$ (see Scheme I and Atallah and Nazer, *Tetrahedron* 38:1793 (1982)).

3-amino-1,2,4-benzotriazines may be prepared either by cyclization of a parent compound (see Scheme II and Arndt, *Chem. Ber.* 3522 (1913)) or by reduction of the monoxide or dioxide as above.

The 3-hydroxy-1,2,4-benzotriazine oxides may be prepared using peroxide and sodium tungstate (Scheme III), a novel synthetic procedure for making the 3-hydroxy-1,4-dioxide compound, or concentrated sulfuric acid and sodium nitrate (Scheme IV).

Scheme I

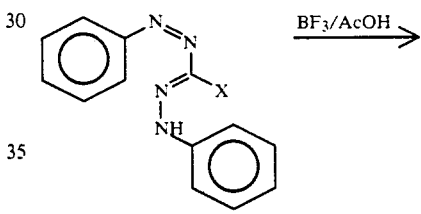

Scheme II

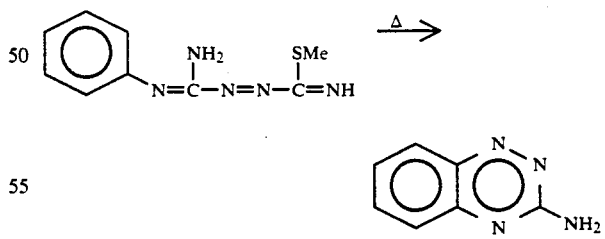

Scheme III

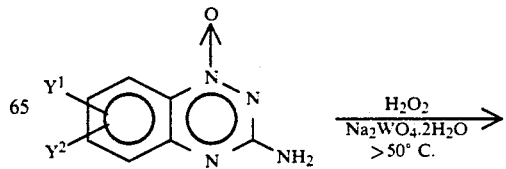

-continued

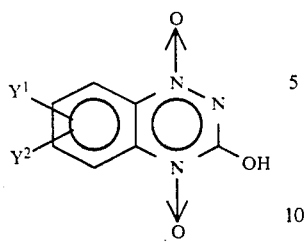

Scheme IV

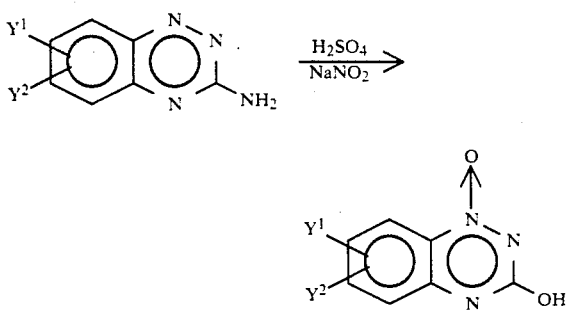

The invention also encompasses a novel method of preparing 1,2,4-benzotriazine oxides unsubstituted at the 3 position (sometimes referred to herein as the "3-desamino" compounds). The novel synthesis involves reductive deamination of the corresponding 3-amino structure. In contrast to prior methods of synthesizing 3-desamino-1,2,4-benzotriazine oxides, the present method enables a simple, straightforward one-step method which gives the desired product in a high yield. The method involves treating a 1,2,4-benzotriazine oxide of Formula (I), wherein X is NH$_2$, with a lower alkyl nitrite under reductive deaminating conditions. By "reductive deaminating conditions" is meant reaction conditions which will give rise to at least about 10%, preferably at least about 50%, of the desired 3-unsubstituted reaction product. A preferred lower alkyl nitrite for use in said method is t-butyl nitrite. Exemplary reductive deaminating conditions involve reaction in a compatible solvent, e.g., dimethyl formamide, at a temperature of at least about 60° C, typically at a temperature in the range of 60°-65° C. This reaction is illustrated generally at Scheme V, and is exemplified in Examples 12-15 herein.

Scheme V

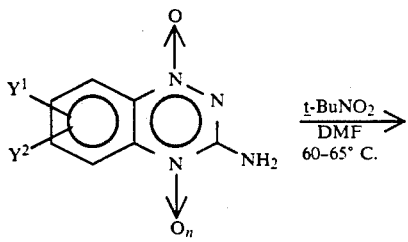

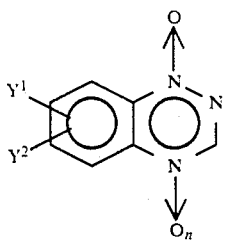

C. Formulation and Administration

As demonstrated below, the oxidized benzotriazines of the invention may be used to radiosensitize or selectively kill hypoxic tumor cells in warm-blooded animal hosts. A way in which they may be used is in con3unction with agents known to selectively create hypoxia in tumors. Such methods include the use of antihypertensive drugs such as hydralazine, or agents which affect the amount of oxygen carried by the blood. While these compounds will typically be used in cancer therapy of human patients, they may be used to kill hypoxic tumor cells in other warm blooded animal species such as other primates, farm animals such as cattle, and sports animals and pets such as horses, dogs, and cats.

Hypoxia is believed to be associated with all types of solid malignant neoplasms. The compounds of the invention may, therefore, be used to radiosensitize or to kill neoplastic epithelial cells, endothelial cells, connective tissue cells, bone cells, muscle cells, nerve cells, and brain cells. Examples of carcinomas and sarcomas include carcinomas such as epithelial cell, acidic cell, alveolar cell, basal cell, basal squamous cell, cervical, renal, liver, Hurthle, Lucke, mucinous and Walker, and sarcomas such as Abernathy's, alveolar soft part, angiolithic, botyroid, encephaloid, endometria stroma, Ewing's fascicular, giant cell, lymphatic, Jensen's, juxtacortical osteogenic, Kaposi's, medullary, and synovial. Specific examples of tumors that have been sensitized with other radiosensitizers are reported in Adams, G.E., *Cancer: A Comprehensive Treatise* (F. Becker, Ed) vol 6, pp 81-223, Plenum, New York, 1977.

The compounds may be administered to patients orally or parenterally (intravenously, subcutaneously, intramuscularly, intraspinally, intraperitoneally, and the like). When administered parenterally the compounds will normally be formulated in a unit dosage injectable form (solution, suspension, emulsion) with a pharmaceutically acceptable vehicle. Such vehicles are typically nontoxic and nontherapeutic. Examples of such vehicles are water, aqueous vehicles such as saline, Ringer's solution, dextrose solution, and Hank's solution and nonaqueous vehicles such as fixed oils (e.g., corn, cottonseed, peanut, and sesame), ethyl oleate, and isopropyl myristate. Sterile saline is a preferred vehicle and the compounds are sufficiently water soluble to provide a solution for all foreseeable needs. The vehicle may contain minor amounts of additives such as substances that enhance solubility, isotonicity, and chemical stability, e.g., antioxidants, buffers, and preservatives. When administered orally (or rectally) the compounds will usually be formulated into a unit dosage form such as a tablet, capsule, suppository or cachet. Such formulations typically include a solid, semisolid or liquid carrier or diluent. Exemplary diluents and vehicles are lactose, dextrose, sucrose, sorbitol, mannitol, starches, gum acacia, calcium phosphate, mineral oil, cocoa butter, oil of theobroma, alginates, tragacanth, gelatin, methylcellulose, polyoxyethylene sorbitan monolaurate, methyl hydroxybenzoate, propyl hydroxybenzoate, talc, and magnesium stearate.

The amount of compound administered to the subject is sufficient to radiosensitize or to produce cytotoxicity in the malignant neoplasm to be treated but below that which may elicit toxic effects to normal tissue. This amount will depend upon the type of tumor, the species of the subject being treated, the indicated dosage intended and the weight or body surface of the subject. The radiation may be administered to humans in a variety of different fractionation regimes, i.e., the total radiation dose is given in portions over a period of several days to several weeks. These are most likely to vary from daily (i.e., five times per week) doses for up to six weeks, to once weekly doses for four to six weeks. An individual dose of the benzotriazine will be given before or after each radiation treatment and is likely to be in the range of 0.01 to 20 mmol/kg and usually in the range of 0.1 to 2 mmol/kg. In these treatment regimens, each radiation dose is typically 1–5 Gy, preferably, less than 2.5 Gy and more preferably 2–2.5Gy. Typically, one dose of radiation is administered per day although 2 or more might be used if tolerated by the patient It has now been found that the compounds disclosed herein as radiosensitizers, particularly 3-amino-1,2,4-benzotriazine 1,4-dioxide, both sensitize tumors to radiation without increasing the sensitivity of normal skin, and work in highly fractionated radiation regimens. As demonstrated in Example 22 herein, pre- or post-irradiation treatment of cells with, for example, 3-amino-1,2,4-benzotriazine 1,4-dioxide, under hypoxic conditions, radiosensitizes cells even when the drug is not present during the radiation exposure and the cells are aerobic.

For use as selective cytotoxic agents, the compounds of the invention can be administered alone, with radiation or other cancer cytotoxic agents, with vasoactive drugs (e.g., hydralazine), or under other conditions which reduce the amount of available oxygen carried by the blood such as anemia or drugs which increase the binding of oxygen to hemoglobin, all of which can enhance selectively the degree of hypoxia in the tumor.

EXAMPLES

The following examples further illustrate the compounds of the invention and methods for synthesizing and using them, and are not intended to limit the invention in any manner.

Experimental: All reactions were carried out in flame-dried glassware and under a blanket of Argon. t-butyl nitrite (90%) was purchased from the Aldrich Chemical Company. Dimethylformamide was distilled from calcium hydride. 7-Nitro-3-amino-1,2,4-benzotriazine-3-amine 1-oxide was purchased from Parish Chemical Company, trifluoroacetic anhydride, N,N-diethylethylenediamine, N,N-diethylpropylenediamine and sodium tungstate dihydrate were purchased from Aldrich Chemical Company and 70% hydrogen peroxide was a gift from Interox America. All reactants were used without further purification. Flash chromatography was carried out on E. Merck 230–400 mesh silica gel under a positive pressure of argon. NMR spectra were obtained on a Varian XL-400 or Jeol FX90Q spectrometer and in $d_6$-acetone, $d_4$-methanol, or $d_6$-dimethyl sulfoxide, as indicated, and are reported relative to the central peak in the appropriate multiplet (2.04, 3.30, and 2.49 ppm, respectively), UV spectra were obtained on a Perkin-Elmer 552 spectrophotometer in 95% ethanol, mass spectra were obtained on an LKB 9000 mass spectrometer, and elemental analyses were carried out by Desert Analytics, Tucson, AZ.

EXAMPLE 1

Preparation of 3-Hydroxy-1,2,4-Benzotriazine 1,4-Dioxide

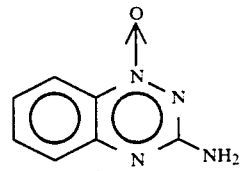

A stirred mixture of 1.50g (9.25 mmole) of 3-amino-1,2,4-benzotriazine 1-oxide (1), 100.0 ml acid, and 30.0 ml of 30% hydrogen peroxide was treated with 3.05 g (9.25 mmole) of $Na_2WO_4 \cdot 2H_2O$. The mixture was stirred in an oil bath at 60° C. for 4 days. The yellowish orange mixture was cooled was cooled to about 30° and filtered to remove a light yellow non-UV absorbing solid. The orange solution of hydrogen peroxide in acetic acid was evaporated to semi-dryness carefully with several additions of water and acetic acid to remove most of the peroxide. The concentrated solution was allowed to stand at room temperature to afford four crops of an orange solid, 0.87 g (42% yield of the sodium salt of 2). $UV_{max}$ (20% $CH_3OH/H_2O$): 262.2 (e 39,460); 477 (e7,030). IR (neat): 3530 $\mu$, 3150 $\mu$, 2650 $\mu$, 2180 $\mu$ and 1635 $\mu$. Anal. (calculated for the sodium salt): $C_7H_4N_3O_3Na \cdot 1.25H_2O$, 223.64: C,37.6; H,2.93; N, 18.79. Found: C, 37.8; H,2.75; N,18.65.

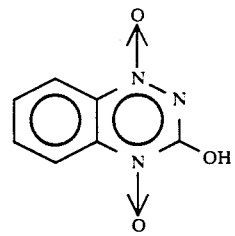

EXAMPLE 2

Preparation of 3-Amino-7-Trifluoromethyl-1,2,4-Benzotriazine 1-Oxide:

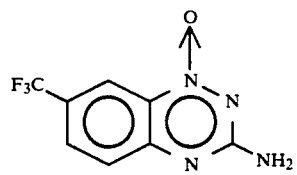

A mixture of 4-chloro-3-nitrobenzotrifluoride (Aldrich, 2.70 g, 12.9 mmole) and cyanamide dihydrochloride (2.75 g, 24 mmole) (previously prepared by treating an ether solution of cyanamide with HCl gas and collecting the precipitated solid) was heated at 140° C. for 1 h. The residue was treated with 2N NaOH (45 ml), heated for a further 5 min, and then allowed to cool. The precipitate was collected, washed with H$_2$O, dried, and triturated with acetone-toluene to yield 1.32 g (45%) of 3 as a light yellow solid M.P. 301°-302°, TLC R$_f$ 0.60 (9:1 methylene chloride: methanol on silica gel plates). Mass. Spec.: M$^+$ = 230 (q = 100).

EXAMPLE 3

Preparation of 3-Amino-7-Decyl-1,2,4-Benzotriazine 1-Oxide

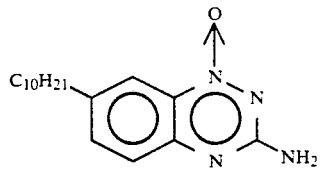

4

Preparation of 4-(1-decyl)-2-nitroaniline: Acetic anhydride (400 ml) was added over a 30-minute period to a stirred solution of 4-decylaniline (Aldrich, 80 g, 0.34 mole) in hexanes (2.4 l). After stirring for 1h, the mixture was cooled and treated over 30 min. at 5°-10° C. with 70% nitric acid (34 ml). Stirring was continued at 5°-10° C.. for 1h and at 25° C. for 16h. The mixture was diluted with H$_2$O(1 l), stirred for 5h, poured into an open dish and allowed to stand for 16h. After further dilution with H$_2$O (1.5 l), the solid was collected and recrystallized from an 85% ethanol solution (in water) to give 92 g (84%) of the intermediate as an orange solid, m.p. 64° C.

A solution (100 ml) of 85% KOH (19 g, 0.288 mole) in H$_2$O was combined with a suspension of 4-(1-decyl)-2-nitroaniline (89 g, 0.28 mole), prepared above, in methanol (900 ml). The mixture was stirred for 6h, neutralized to pH 7-8 with concentrated HCl, and evaporated in vacuo to near dryness. After dilution with H$_2$O (400 ml), the solid was collected and air-dried to give 77 g (100%) of the intermediate as an orange solid, m.p. 59° C.

1.0 g (8.7 mmole) of cyanamide dihydrochloride (previously prepared for use by treating an ether solution of cyanamide with HCl gas and collecting the precipitated solid) was added portionwise over 10 min to a preheated melt (190° C.) of 4-(1-decyl)-2-nitroaniline prepared in the preceding step (500 mg, 1.8 mmole). The reaction mixture was heated at 190° C. for 5 min, cooled to 25° C., treated with 6N KOH (10 ml), and heated at 90°-95° C. for 1h. After cooling to 25° C., the solid was collected, washed with H$_2$O and ethanol and air-dried to give 0.25 g (46%) of compound 4 as a light yellow solid, m.p. 177° C. (dec). Mass. spec. M$^+$ = 285 (q = 100), 302 (q = 13).

EXAMPLE 4

Preparation of 3-Amino-7-Carbamyl-1,2,4-Benzotriazine 1-Oxide

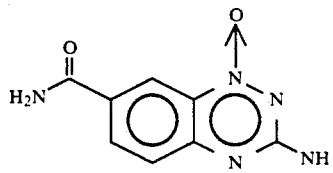

5

Preparation of 4-chloro-3-nitrobenzamide: 20.2 g (0.1 mole) of 4-chloro-3-nitrobenzoic acid (Aldrich) and thionyl chloride (20 ml) were combined, allowed to stand for 16h, and refluxed for 4h to give a clear red solution. The solution was evaporated in vacuo and azeotroped with benzene. The residue was dissolved in acetonitrile (20 ml) and added over 30 min to cold (−10° C.) concentrated ammonium hydroxide (100 ml). After 3h at −10° C. and 16h at 25° C. the mixture was poured into an open dish and allowed to evaporate to dryness. The residue was slurried in H$_2$O and the solid was collected and air-dried to give 19.8 g (98%) of the intermediate as a light yellow solid, m.p. 153° C.

A solution of Na (3.45 g, 0.15 mole ) in ethanol (75 ml) was added to a solution of guanidine hydrochloride (15.8 g, 0.165 mole) in ethanol (75 ml). After 1h the mixture was filtered and the filtrate was combined with a suspension of 4-chloro-3-nitrobenzamide (10 g, 0.05 mole) prepared above, in ethanol (50 ml). The mixture was stirred and refluxed for 16h, cooled to 0°-5° C., and acidified with concentrated HCl (8 ml). The collected solid was combined with K$_2$CO$_3$ (28 g, 0.2 mole) and H$_2$O (40 ml) and the mixture was stirred and heated at 100° C. for 8h. After cooling to 25° C., the solid was collected, washed with H$_2$O, and air-dried. The solid was suspended in boiling ethyl acetate, collected and washed with hot ethyl acetate. The solid was repeatedly suspended in boiling dioxane and collected (6 × 100ml). The combined filtrate was evaporated in vacuo to a solid. The solid was suspended in 95% ethanol, collected and air-dried to give 0.44 g (4.3%) of compound 5 as a light yellow solid, m.p. 300° C. TLC: R$_f$ = 0.23 (methylene chloride: acetone of 2:1, silica gel plates). Mass. Spec.: M$^+$ 205 (q = 100).

EXAMPLE 5

Preparation of 7-Acetyl-3-Amino-1,2,4-Benzotriazine 1-Oxide Oxime

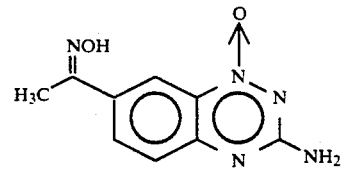

6

A combined mixture of 7-acetyl-3-amino-1,2,4-benzotriazine 1-oxide (prepared in Example 5; 50 mg, 0.25 mmole), hydroxylamine hydrochloride (200 mg, 2.88 mmole), pyridine (1 ml) , and ethanol (1 ml) was heated at 90°-95° C. for 1h and then cooled to 25° C. The mixture was diluted with 95% ethanol (5 ml) and the solid was collected and air-dried to give 30 mg (56%) of compound 6 as a light yellow solid, m.p. 278° C. (dec). TLC: R$_f$ = 0.60 (9:1 methylene chloride: methanol). Mass Spec.: M$^+$ = 219 (q = 100).

EXAMPLE 6

Preparation of 3-Amino-6(7)-Decyl-1,2,4-Benzotriazine 1,4-Dioxide

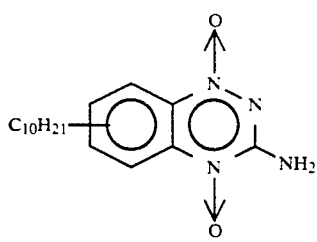

7

5-(1-decyl)-benzofuroxan: A combined mixture of 4-(1-decyl)-2-nitroaniline (77 g, 0.28 mole), 5.25% NaOCl in H$_2$O (476 g, 0.34 mole), 85% KOH (20.3 g, 0.31 mole), nBu$_4$NHSO$_4$ (4.7 g, 0.014 mole), and CH$_2$Cl$_2$ (2.28 l) was stirred rapidly for 6h and diluted with H$_2$O (500 ml) and CH$_2$Cl$_2$ (1 l). The separated organic phase was washed successively with 1N HCl (1 l) and brine (2×1 l)), dried (Na$_2$SO$_4$), and concentrated in vacuo to yield a red oil, 70 g (92%).

A solution of 5-(1-decyl)-benzofuroxan as prepared above (10 g, 0.036 mole) and benzyltriethyl ammonium chloride (0.36 g, 0.0016 mole) in DMSO (180 ml) was treated gradually over several hours with cyanamide (13.0 g, 0.31 mole) and K$_2$CO$_3$ (36.8 g, 0.27 mole). The mixture was stirred for 48h and filtered. The filtrate was diluted with H$_2$O (6 l) and glacial acetic acid (40 ml) and extracted with CH$_2$Cl$_2$ (4×500 ml). The combined organic solution was washed successively with 5% NaHCO$_3$ solution (1×500 ml) and brine (2×500 ml), dried (Na$_2$SO$_4$), and evaporated in vacuo to dryness. The crude product was purified by chromatography on silica gel using CH$_2$Cl$_2$: methanol (98:2) to give 1.8 g (16%) of compound 7 as a red solid, m.p. 155° C. (dec). Mass. Spec.: M$^+$ = 318 (q=4), 285 (q=100).

EXAMPLE 7

Preparation of 1,2,4-Benzotriazine

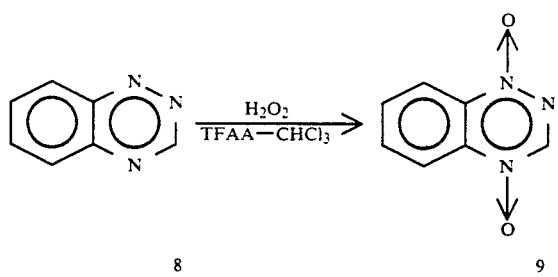

8    9

A mixture of 1.80 g (13.73 mmole of 8, 90% H$_2$O$_2$ (9 ml), trifluoroacetic anhydride (13.5 ml) and Na$_2$WO$_4$.2H$_2$O (12.50 g, 38 mmole) in CHCl$_3$ (170 ml) was stirred at room temperature for 5 days. The reaction mixture was diluted with H$_2$O (100 ml) and extracted with CHCl$_3$ (100 ml). The organic layer was washed with H$_2$O (50 ml), dried (Na$_2$SO$_4$), and the solvent removed in vacuo. The residue was chromatographed on silica gel using EtOAc-CH$_2$Cl$_2$ (1:1) to give 0.30 g (13.4%) of compound 9 as a yellow solid, m.p. 204°-205° C. Anal. Calc'd. for C$_7$H$_5$N$_3$O$_2$(163.13): C, 51.5; H, 3.09; N, 25.76. Found: C, 51.6; H, 3.36; N, 26.01. Mass Spec. M$^+$ = 163 (q TM 100), 147 (q=50). TLC: R$_f$=0.27 (EtOAc-CH$_2$Cl$_2$, 1:1, silica gel plates). IR (nujol): 1600 µ, 1460 µ, 1300 µ, 1230 µ. UV$_{max}$(H$_2$O): 227 (ε 22,900) 252 (ε 12,950); 392 (ε 4,080).

EXAMPLE 8

Preparation of 7-Chloro-3-Hydroxy-1,2,4-Benzotriazine 1,4-Dioxide

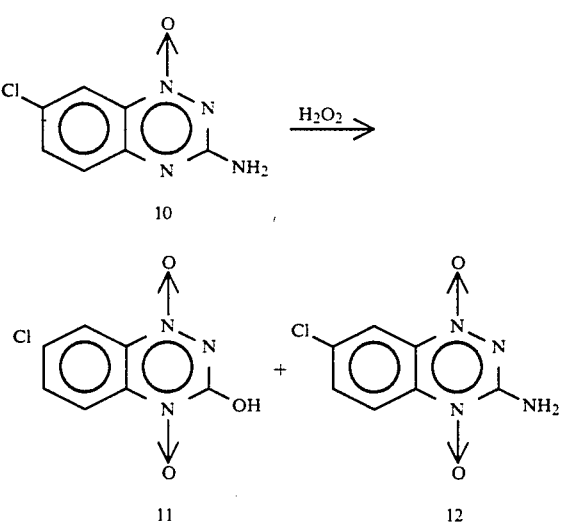

A mixture of 1.50 g (7.63 mmole) of 10 in 100 ml acetic acid was treated with 2.52 g (7.63 mmole) of Na$_2$WO$_4$.2H$_2$O and 30 ml of 30% H$_2$O$_2$. The mixture was stirred and heated for 6 days at 50° C., then slowly evaporated to dryness to remove H$_2$O$_2$. The residue was boiled in 250 ml H$_2$O and filtered to remove about 25 mg of starting material 12. The aqueous solutions were then extracted with 2×250 ml portions of ethyl acetate. A deep red crystalline material that was characterized as 12 by TLC and Mass. Spec. analysis formed in the partitioning mixture above and was collected by filtration to afford 60.0 mg of a yellowish orange solid (3.7% yield), characterized as follows as 12, which showed good solubility in a mixture of hot isopropyl alcohol and water. Mass. Spec.: M$^+$ = 212 q=100)(compound 10); TLC: R$_f$=0.34 (acetone, silica gel plates).

The ethyl acetate solutions above, separated from the H$_2$O layer after the filtration to remove 12, were evaporated to dryness. The residue was then treated with isopropyl alcohol at room temperature to afford a dull orange solid, 0.41 g (25% yield) of 11. Mass. Spec.: M$^+$ = 213 (q=70); TLC: R$_f$=0.22 (acetone, silica gel plates). Compound 11 was characterized as the ammonium salt, C$_7$H$_4$ClN$_3$O$_3$ NH$_3$, m.w. 230.61, as follows. The free acid 11 was dissolved in concentrated NH$_4$OH and then chilled in ice and filtered to remove a trace of insoluble 12. The red filtrate and washings were evaporated to dryness, leaving a reddish-orange solid. The solid was treated with 50 ml of boiling 1,2-dimethoxyethane, collected on a filter and washed with an additional 25 ml of hot 1,2-dimethyl ether. The solid was dried over P$_2$O$_5$ at 56° C./1.0 mm, leaving 0.244 g (87% yield) of 13

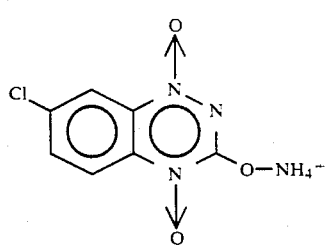

Anal. Calc'd. for $C_7H_4ClN_3O_3NH_3$ (230.61): C, 36.5; H, 3.06; N 24.30 Found: C 36.5; H 3.07; N 23.94 $UV_{max}$ ($H_2O$): 219 ($\epsilon$ 12,580); 265.4 ($\epsilon$ 40,000); 4830486 ($\epsilon$ 6,640).

EXAMPLE 9

Preparation of 7-Nitro-3-Amino-1,2,4-Benzotriazine 1,4-Dioxide

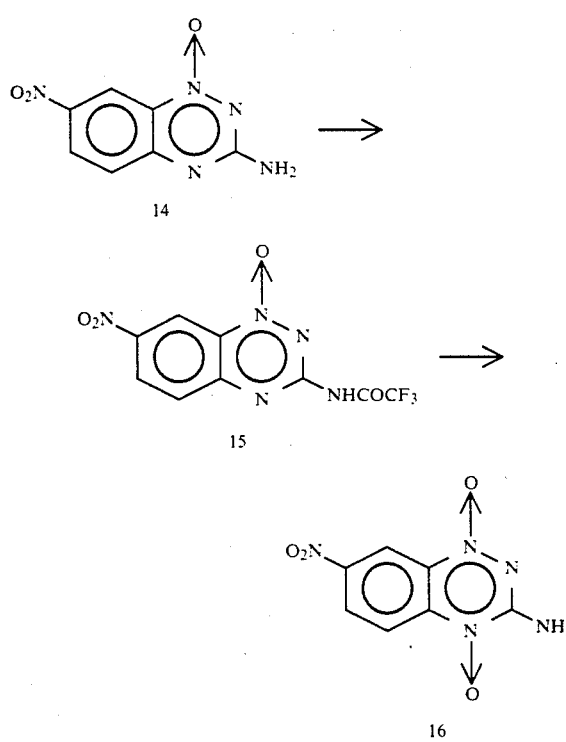

7-Nitro-3-trifluoroacetamido-1,2,4-benzotriazine 1-oxide (15): A solution of 7-nitro-3-amino-1,2,4-benzotriazine 1-oxide (14) (4.00 g, 19.3 mmol; Parish Chemical Co.), $CHCl_3$ (125 ml) and trifluoroacetic anhydride (12.0 ml, 85.0 mmol) was stirred at room temperature for 44 hr. The resultant light yellow solid was filtered, washed with $CHCl_3$ (50 ml) and dried to give 5.35 g (91% yield) of the product as a yellow solid. Anal. Calc'd. for $C_9H_4F_3N_5O_4$: C, 35.7; H, 1.33; N, 23.10. Found: C, 35.7; H, 1.23; N, 23.06.

7-Nitro-3-amino-1,2,4-benzotriazine 1,4-oxide (16): To a stirred solution of 7-nitro-3-trifluoroacetamido-1,2,4-benzotriazine 1-oxide prepared above (15) (2.50 g, 8.25 mmol) in $CHCl_3$ (200 ml) was added $Na_2WO_4.2H_2O$ (90 mg, 0.273 mmol) followed by 70% $H_2O_2$ (10 ml). After 15 min the solution was treated with trifluoroacetic anhydride (8.0 ml, 56.7 mmol) and stirring was continued at room temperature for 64 hr. The reaction mixture was chromatographed (EtOAc, 20% MeOH/acetone, and finally 20% DMF/acetone) then recrystallized in acetone to give 1.20 g (65% yield) of the product (16) as an orange solid, mp 286°–288° C. (dec.). UV: $\delta$ 259, 300, 345, 387, 472. Anal. Calc'd. for $C_7H_5N_5O_4$ C, 37.70; H, 2.26; N, 31.39. Found: C, 7.70; H, 2.13; N, 30.94.

EXAMPLE 10

Preparation of 3-(3-N,N-Diethylaminopropylamino)-1,2,4-Benzotriazine 1,4-Dioxide

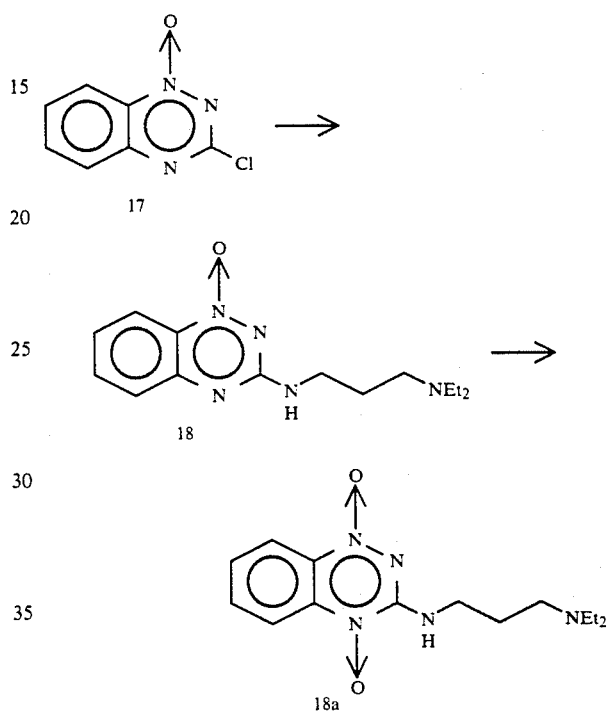

3-(3-N,N-diethylaminopropylamino)-1,2,4-benzotriazine 1-oxide (18): A solution of 3-chloro-1,2,4-benzotriazine 1-oxide (17) (3.0 g, 16.5 mmol) (produced by the method of Sasse et al., U.S. Pat. No. 4,289,771) in $CH_2Cl_2$ (100 ml) was treated with N,N-diethylpropylenediamine (9.5 ml, 88.3 mmol). After 20 hr at room temperature the mixture was diluted with 1,2-dichloroethane (50 ml) and washed successively with $Na_2CO_3$ and $H_2O$. The yellow solution was dried ($Na_2SO_4$), filtered and evaporated in vacuo to give 3.93 g (87% yield) of the product as a yellow solid. Recrystallization (ether/petroleum ether) yielded pure material, mp 47°–48° C. Anal Calc'd for $C_{14}H_{21}N_5O$ (18): C, 61.10; H, 7.69; N, 25.44. Found: C, 61.30; H, 7.80; N, 25.61.

3-(3-N,N-diethylaminopropylamino)-1,2,4-benzotriazine 1,4-dioxide (18a): To a stirred solution . of 3-(3-N,N-diethylaminopropylamino)-1,2,4-benzotriazine 1-oxide 18 prepared as above (1.60 g, 6.10 mmol) in $CHCl_3$ (50 ml) was added trifluoroacetic anhydride (22.0 ml). After 15 min the mixture was cooled to $-10°$ C., 70% $H_2O_2$ (10 ml) added and then stirred at room temperature for 20 days. The reaction mixture was dried ($Na_2SO_4$), filtered and evaporated to dryness. The residue was dissolved in saturated $NaHCO_3$ solution (50 ml) and extracted with $CH_2Cl_2$ (3×150 ml). The organic layer was dried ($Na_2SO_4$), filtered and evaporated to give the product 18a, 0.51 g (29% yield) as a red solid, mp 92°-94° C. NMR: δ (400 MHz, CDCl₃) 1.11 (6H, t, J=7.1 Hz, CH₃), 1.84-1.90 (2H, m, H-2'), 2.48-2.64 (4H, m, NCH₂CH₃ and H-3'), 3.68 (2H, br t, J=5.5 Hz, H-1'), 7.46 (1H, ddd, J=7.1, 7.0 and 1.2 Hz, H-6), 7.84, ddd, J=7.0, 6.9 and 1.2 Hz, H-7), 8.31 (2H, m, H-5 and 8), 8.80 (1H, br s, NH). UV: δ 220, 270, 476. Anal. Calc'd. for C₁₄H₂₁N₅O₂. (⅜ H₂O): C, 56.50; H, 7.34; N, 23.55. Found: C, 56.90; H, 7.15; N, 23.40.

EXAMPLE 11

Preparation of
7-Nitro-3-(2-N,N-Diethylaminoethylamino)-1,2,4-Benzotriazine 1,4 Dioxide

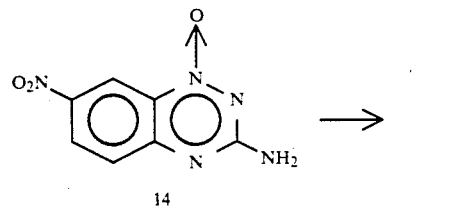

14

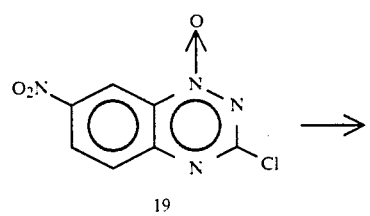

19

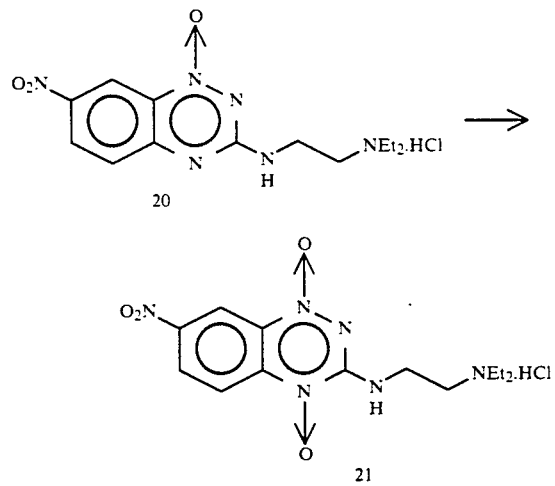

7-nitro-3-(2-N,N-diethylaminoethylamino)-1,2,4-benzotriazine 1-oxide hydrochloride (20): A solution of 7-nitro-3-chloro-1,2,4-benzotriazine 1-oxide (19) (1.60 g, 7.06 mmol) (prepared as generally shown in Sasse et al., U.S. Pat. 4,289,771, with (a) NaNO₂ and H₂SO₄ at 40° C., followed by (b) chlorination with POCl₃ at 106° C.) in CH₂Cl₂ (50 ml) was treated with N,N-diethylethylenediamine (6.0 ml, 42.7 mmol). After 6 hr at room temperature the mixture was evaporated to dryness under high vacuum at 60° C. The yellow solid was stirred in 20% iPrOH/ether (150 ml) for 5 hr, filtered, washed with iPrOH then petroleum ether and dried (80° C./1.0 mmHg) to give 1.80 g (74% yield) of the product 20 as yellow needle crystals. NMR δ (90 MHz, d₆-DMSO/d₄-MeOH) 1.25 (6H, t, J=6.0 Hz, CH₃), 3.25 (6H, m, NCH₂), 3.82 (2H, m, H-1'), 7.74 (1H, d, J=7.0 Hz, H-5), 8.52 (1H, dd, J=7.0 and 2.0 Hz, H-6), 8.91 (1H, d, J=2.0 Hz, H-8).

7-nitro-3-(2-N,N-diethylaminoethylamino)-1,2,4-benzotriazine 1,4-dioxide hydrochloride (21). To a stirred solution of 7-nitro-3-(2-N,N-diethylaminoethylamino)-1,2,4-benzotriazine 1-oxide hydrochloride (20; prepared as described above) (0.50 g, 1.46 mmol) in CHCl₃ (50 ml) at 0° C. was added trifluoroacetic anhydride (9.0 ml). After 30 min 70% H₂O₂ (4.0 ml) was added and the mixture stirred at room temperature for 3 days, then dried (Na₂SO₄), filtered, and evaporated in vacuo to dryness to give the trifluoroacetate salt 0.67 g (45% yield). This product was dissolved in saturated NaHCO₃ solution (30 ml) and extracted with CH₂Cl₂ (3×30 ml). The dichloromethane was washed with H₂O, dried (Na₂SO₄), filtered, saturated with gaseous HCl and evaporated to dryness to give 0.35 g (63% yield, 28% overall) of the product as a red solid, m.p. 194°-195° C. UV: λ 260, 306, 388, 479. Anal. Calc'd. for C₁₃H₁₈N₆O₄.HCl: C, 43.50; H, 5.34; N, 23.43. Found: C, 43.20; H, 5.37; N, 23.11.

The following Examples 12-15 are directed to reductive deamination reactions for preparing compounds of Formula (I) which are unsubstituted at the 3-position, i.e., wherein the substituent "X" is hydrogen.

EXAMPLE 12

Preparation of 1,2,4-Benzotriazine 1,4-Dioxide by Reductive Deamination of
3-Amino-1,2,4-Benzotriazine

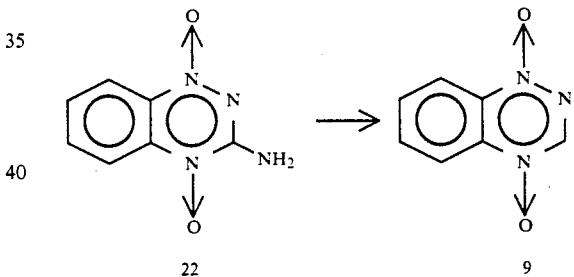

22          9

To a rapidly stirred solution of t-butyl nitrite (867 mg, 1.0 ml, 8.41 mmol) in DMF (20 ml) at 60°-65° C. was added 3-amino-1,2,4-benzotriazine 1,4-dioxide ("SR 4233") (500 mg, 2.81 mmol) (prepared by the method of Seng et al., Angew. Chem. Internat. Edit. 11 (1972)) in small portions over 5 min. Following the addition, and subsidence of the concomitant effervescence (approx. 5 min), the solution was cooled and reduced under high vacuum to a dark waxy solid. Flash chromatography (30% EtOAc/CH₂Cl₂) gave a yellow solid, mp 188°-189.5° C. (dec.), which was recrystallized from methanol to give 195 mg (43% yield) of the product 9 as bright yellow platelets, mp 192°-194° C. (dec.). NMR: (400 MHz, d6-acetone) 8.04 (1 H, ddd, J=8.5, 7, 1.5 Hz), 8.15 (1 H, ddd, J=8.5, 7, 1.5 Hz), 8.42 (1 H, dd, J=8.5, 1.5 Hz), 8.43 (1 H, dd, J=8.5, 1.5 Hz) 9.05 (1 H, s, H-3). UV: λ 405, 300, 225. MS, m/z (relative +), 147(13), 136(19), intensity) 164(9), 163(100, M+), 147(13), 136(19), 90(7), 78(27), 76(26), 75(8), 64(9), 63(10), 52(12), 51(48), 50(28), 38(8), 37(5), 30(18), 28(6), 27(7). Anal Calc'd. for C₇H₅N₃O₂: C, 51.54; H, 3.09; N, 25.76. Found: C, 51.42; H, 3.02; N, 25.66.

EXAMPLE 13

Preparation of 7-Allyloxy-1,2,4-Benzotriazine 1,4-Dioxide Via Reductive Deamination

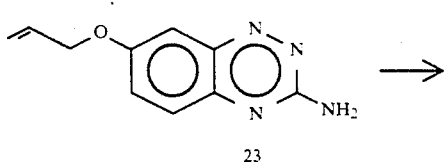

23

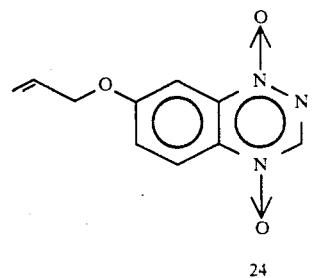

24

7-Allyloxy-1,2,4-benzotriazine 1,4-dioxide 24: To a stirred solution of t-butyl nitrite (271 mg, 0.312 ml, 2.63 mmol) in DMF (15 ml) at 60°–65° C. was added 7-allyloxy-3-amino-1,2,4-benzotriazine- 1,4-dioxide 23 (205 mg, 0.875 mmol) in small portions over 5 min. After 30 min additional t-butyl nitrite (271 mg, 0.312 ml, 2.63 mmol) was added, and shortly thereafter the deep red solution effervesced and lightened appreciably in color over a period of a few minutes. After an additional 30 min the resultant orange solution was reduced under vacuum to a brown solid which was sequentially flash chromatographed (10% EtOAc/CH$_2$Cl$_2$) and crystallized (CH$_2$Cl$_2$/petroleum ether) to give 72 mg (38% yield) of the product 24 as light orange crystals, mp 147°–148° C. NMR: δ (400 MHz, d$_6$-acetone) 4.89 (2 H, ddd, H-1', J$_{1',2'}$=5.5, J$_{1',3'cis}$=J$_{1',3'trans}$=1.5 Hz), 5.36 (1 H, ddd, H-3', J$_{3',2'cis}$=10.5, J$_{3',3'}$=3, J$_{3',1'}$=1.5 Hz), 5.52 (1 H, ddd, H-3', J$_{3',2'trans}$=17.5, J$_{3',3'}$=3, J$_{3',1'}$=1.5 Hz), 6.14 (1 H, ddt, H-2', J$_{2',3'cis}$=10.5, J$_{2',1'}$=5.5 Hz), 7.70 (1 H, d, H-8, J$_{8,6}$=2.5 Hz), 7.74 (1 H, dd, H-6, J$_{6,5}$=9.5, J$_{6,8}$=2.5 Hz), 8.33 (1 H, d, H-5, J$_{5,6}$=9.5 Hz), 8.93 (1 H, s, H-3). UV: λ 425, 410, 365, 355, 320, 245, 200. MS m/z/ (relative intensity) 220(4), 219(34 M$^+$), 103(4), 77(4), 75(4), 63(13), 62(4), 42(3), 41(100), 39(16). Anal. Calc'd for C$_{10}$H$_9$N$_3$O$_3$: C, 54.79; H, 4.14; N, 19.17. Found: C, 54.73; H, 4.16; N. 19.15.

EXAMPLE 14

Preparation of 7-(3-N-Ethylacetamido-2-acetoxypropoxy)-1,2,4-Benzotriazine 1,4-Dioxide Reductive Amination

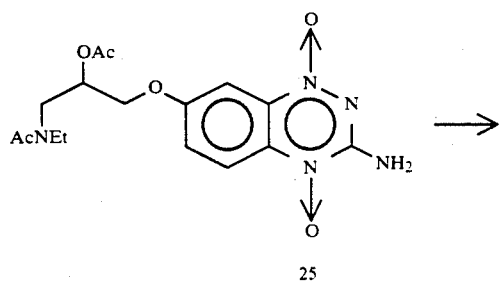

25

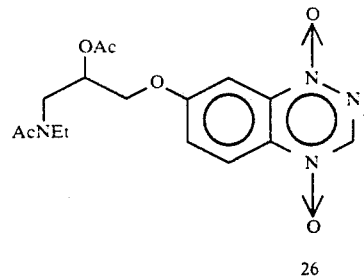

26

To a stirred solution of t-butyl nitrite (185 mg, 1.79 mmol) in DMF (5 ml) at 60° C. was added via syringe a solution of 7-(3-N-ethylacetamido-2-acetoxypropoxy)-3-amino-1,2,4-benzotriazine 1,4-dioxide (25) (125 mg, 0.329 mmol) in DMF (5 ml) over a period of 1 min. After 5 min additional t-butyl nitrite (217 mg, 2.10 mmol) was added and an immediate reaction occurred, as evidenced by the evolution of a gas and a change in color of the solution from red to light orange. After an additional 10 min the solution was stripped to a yellow/brown solid and eluted through silica gel with 5% MeOH/CH$_2$Cl$_2$ to give CH$_2$Cl$_2$/ligroin gave 90 mg yellow solid (75% yield), mp 179°–180.5° C. NMR: δ (400 MHz, d$_4$-methanol, mixture of rotamers, ratio approx. 2:1) 1.12, 1.22 (t's, 1:2, 3 H total, J=7 Hz), 2.06, 2.07 (s's, 2:1, 3 H total), 2.11, 4.34–4.48 (m, 2 H), 5.48–5.58 (m, 1 H), 7.76–7.86 (m, 2 H), 8.36–8.42 (m, 1 H), 9.04, 9.06 (s's, 2:1, 1 H total). UV: λ 420, 405, 365, 350, 315, 240, 200. MS: m/z (relative intensity) 365(0.5), 364(1.4, M$^+$), 349(0.5), 348(1.1), 347(0.5), 332(1.2), 331(3.6), 187(7), 186(66), 102(6), 100(21), 84(30), 63(6), 58(100), 56(8), 43(65), 42(9), 41(5), 30(14), 29(5), 28(8).

EXAMPLE 15

Preparation of 7-Nitro-1,2,4-Benzotriazine 1,4-Dioxide via Reductive Deamination

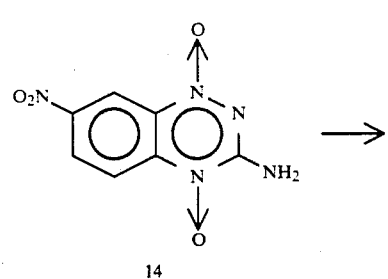

14

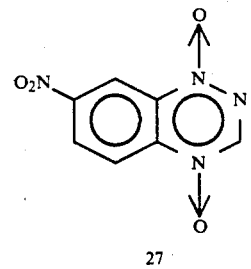

27

To a stirred solution of t-butyl nitrite (88 mg, 0.85 mmol) in DMF (5 ml) at 60° C. was added 7-nitro-3-amino-1,2,4-benzotriazine 1,4-dioxide (14) (38 mg, 0.17 mmol). After 30 min the addition of further t-butyl nitrite (175 mg, 1.70 mmol) to the dark red slurry was immediately followed by a change in coloration and effervescence. After an additional 10 min the orange solution was reduced to a red solid in vacuo and chromatographed with 1% AcOH/CH$_2$Cl$_2$ to give 3 mg of the product 27 as a yellow solid (10% yield). NMR δ (90 MHz, d$_6$-dimethyl sulfoxide) 7.68 (d, 1H, J=9.2 Hz), 7.92 (dd, 1H, J=9.2, 2.2 Hz), 8.10 (d, 1H, J=2.2 Hz), 8.65 (s, 1H)). UV: λ 420, 310, 240, 205. MS:m/z (relative intensity) 209 (9), 208 (100, M+), 192 (54), 181 (14), 162 (16), 105 (9), 77 (28), 75 (52), 74 (27), 63 (21), 62 (16), 30 (77), 18 (26).

EXAMPLE 16

In Vivo Assay for Activity in Combination with Radiation

Compounds of the invention were tested in vivo for activity by the assay of Brown, J. M., *Radiation Res* (1975) 64:633-47, incorporated herein by reference. For this assay, SCCVII carcinomas in female C$_3$H mice weighing 20-25 g were used. These mice were bred under specific pathogen-free conditions and were 3-4 months old at the beginning of each experiment. The SCCVII tumor was grown intradermally in the flank from an inoculation of $2 \times 10^5$ tumor cells taken from the 2nd-8th in vitro passage of the tumor cells after removal from the previous in vivo tumor. Two tumors per mouse were implanted, and were used as subject tumors when they reached a volume of approximately 100 ml. At this point the tumors contained approximately 20% hypoxic cells.

Figure 2:
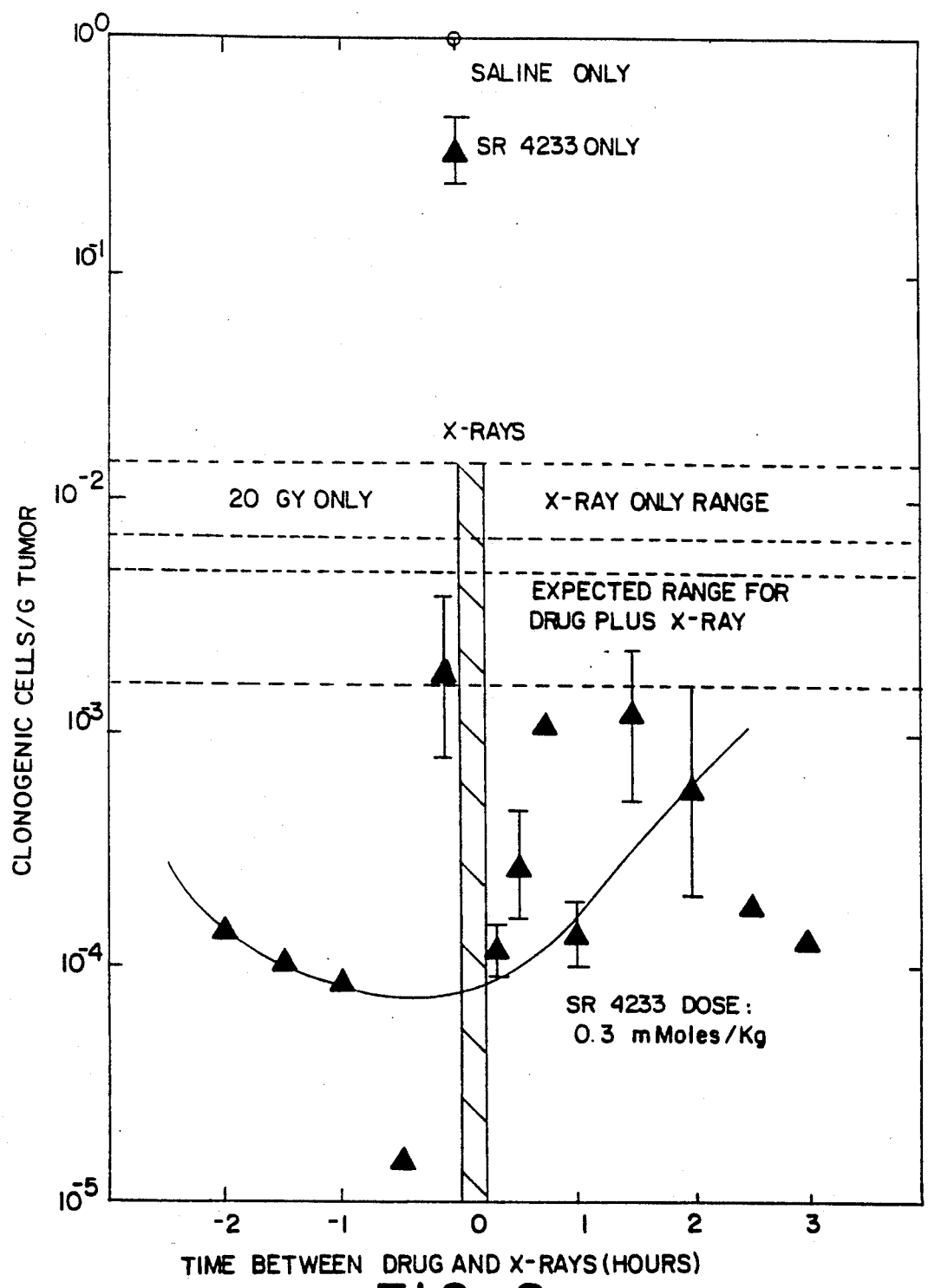
FIG. 2 shows the in vivo efficacy of 3-amino-1,2,4-benzotriazine 1,4-dioxide in enhancing the killing of tumor cells when combined with radiation.

The test compound was tested at a fixed injected dose of either 5 mmol/kg or ⅔ of the LD$_{50}$ (whichever was lower). Suitable controls of test compound-injected but nonirradiated and saline-injected and irradiated mice were also included. A fixed radiation dose of 20 Gy was applied at variable intervals of 2 hr after to 3 hr before injection of the drug. By using these intervals, the results give an indication of both the optimum irradiation time and the extent of extra cell killing compared to radiation alone. The results of such time-course experiments using 3-amino-1,2,4-benzotriazine 1,4-dioxide are shown in FIG. 2. They show enhanced cell killing compared to radiation only, more than would have been expected on the basis of additivity of the two individual cytotoxicities. The similar increased cytotoxicity when the drug is given before or after radiation indicates selective toxicity to the hypoxic cells rather than a radiosensitizing effect of the benzotriazine dioxide.

Irradiation of the SCCVII tumors was done by irradiating nonanaesthetized tumor-bearing mice in a Plexiglas box. Irradiation conditions were 250 kVp X-rays, 15 mA, FSC 33 cm, added filtration of 0.35 mm Cu, half value layer 1.3 mm Cu, and a dose rate of 317 rad/min.

The amount of cell killing was judged by survival rate of dissected and cultured tumor cells as follows. The tumor-bearing mice were killed 24 hr after irradiation, and tumors were dissected from the skin, cut into several pieces, and made into a fine brei by high-speed chopping with a razor blade attached to a jigsaw. The brei was added to 30 ml of Hank's buffered salt solution (HBSS) containing 0.02% DNase, 0.05% promase, and 0.02% collagenase. The suspension was stirred for 30 min at 37° C., filtered, and centrifuged at 1,600 rmp for 10 min at 4° C. The cell pellet was resuspended in complete Waymouth's medium plus 15% fetal calf serum (FCS) and an aliquot mixed with trypan blue and counted with the use of a hemacytometer. Suitable dilutions of this serum plated into 60- or 100-mm polystyrene petri dishes (Lux Scientific Corp) in 5 or 15 ml of medium. After incubation for 13 days, the colonies were fixed and stained, and those containing 50 cells or more were counted. The dilution yielding an average count of 25-100 colonies in a 60 mm dish was used in calculation of results.

EXAMPLE 17

Cytotoxicity Test

Cytotoxicity tests were carried out using 3-amino-1,2,4-benzotriazine 1,4-dioxide and a variety of aerobic and hypoxic cells in culture (human, mouse, and hamster). The cells in spinner flasks were gassed for one hour at 37° C. with either air or nitrogen containing 5% CO$_2$ prior to adding the specified amounts of the drug. FIGS. 1A, 1B and 1C show the results for cell survival of mouse, hamster and human cells at various concentrations of 3-amino-1,2,4-benzotriazine 1,4-dioxide. It was found that only 1 to 2% of the drug concentration under aerobic conditions was required to get equal cell killing under hypoxia. This ratio of selective hypoxic toxicity (50-100) is higher than that for any compound so far reported in the literature.

EXAMPLE 18

Determination of LD$_{50}$

LD$_{50}$ is determined in BALB/c female mice (weighing 20-25 g) following intraperitoneal (ip) injection, unless the compound tested has low lipophilicity and is very soluble, wherein intravenous (iv) administration is used. LD$_{50}$ values at 1, 2, 5, and 60 days are determined by administering graded doses of the drug dissolved in physiological saline immediately prior to injection.

EXAMPLE 19

The results of assays to determine the concentration of drug necessary to produce a sensitizer enhancement ratio of 1.6 of hypoxic cells in culture are as follows:

| Compound | C$_{1.6}$ (mM) |
|---|---|
| 7-chloro-3-amino-1,2,4-benzotriazine 1-oxide | 3.3 |
| 6(7)-methoxy-3-amino-1,2,4-benzotriazine 1,4-dioxide | ~1.0 |
| 3-hydroxy-1,2,4-benzotriazine 1,4-dioxide | ~2.0 |

Modifications of the above described modes for carrying out the invention that are apparent to those of skill in the chemical, pharmaceutical, medical, and related arts are intended to be within the scope of the following claims.

EXAMPLE 20

Enhanced Tumor Cell Toxicity Using Hydralazine

Figure 3:
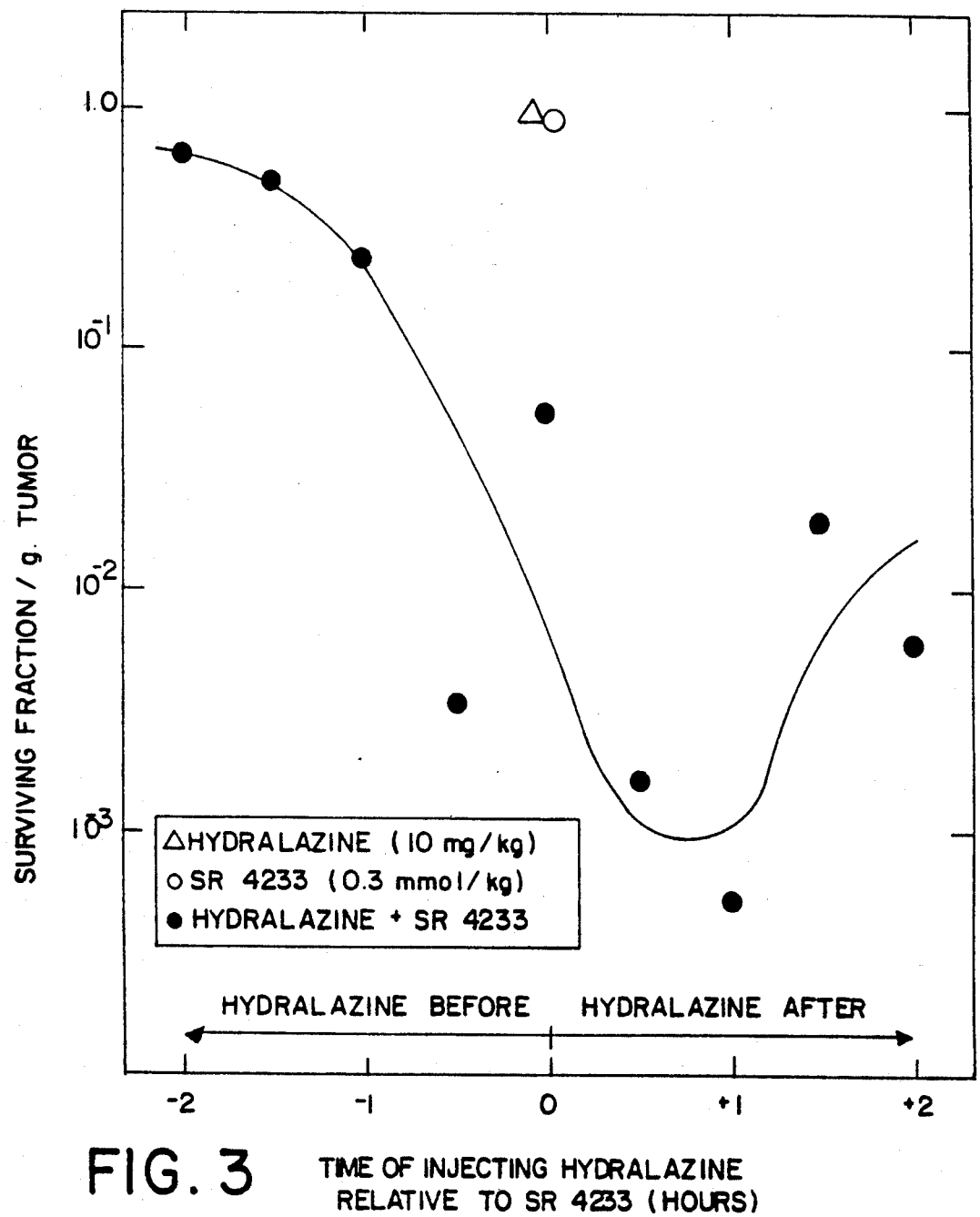
FIG. 3 shows the killing of tumor cells in vivo by 3-amino-1,2,4-benzotriazine 1,4-dioxide when the tumor has been made hypoxic by the intraperitoneal administration of the antihypertensive drug hydralazine.

Hydralazine is an antihypertensive drug which acts by relaxing the smooth muscle around blood vessels. This has the effect of preferentially shunting blood flow into normal tissues and away from tumors, which process produces immediate hypoxia in the tumors. If 3-amino-1,2,4-benzotriazine 1,4-dioxide is given in conjunction with this agent, there is a massive increase in tumor cell killing. In this experiment, neither hydralazine nor the aforementioned benzotriazine compound produced any significant cell killing in the SCCVII tumor, whereas the combination of the two reduced survival by a factor of $10^3$ (i e., only 1 cell in every 100 was left viable). The experimental procedures are the same as described in Example 9, and the results are shown in FIG. 3.

EXAMPLE 21

Physicochemical and Biological Properties of Some 1,2,4-Benzotriazine 1,4-Dioxides The following table sets forth various properties of compounds 22, 14, 18a, and 21 as determined by the inventors herein:

| Cpd. | Mol. Wt. | Solubility (mM) | Log P[a] | $E_{\frac{1}{2}}^{b}$ (mV) | RHT[c] | HCR[d] | LD$_{50}$[e] |
|---|---|---|---|---|---|---|---|
| 22 | 178.2 | 13.50 | −0.32 | −332 | 1 | 100 | 0.50 |
| 14 | 223.2 | 2.00 | −0.97 | −133 | 2 | 140 | 1.00 |
| 18a | 291.4 | >181 | −1.34 | −348 | 3 | 100 | 0.25 |
| 21 | 358.9 | 96.40 | −0.20 | −140 | 3 | 211 | 0.40 | a.) Log of the octanol-water partition coefficient as measured by the method of Fujita et al., *J. Amer. Chem. Soc.* 86:5175 (1964), using pH 7.4 buffer.

b.) Polarographic half-wave reduction potentials measured in Britton & Robinson pH 7.4 buffer using a dropping mercury electrode.

c.) Relative Hypoxic Cytoxicity: Ratio of equitoxic concentrations of 22:analog for HA-1 cells attached, under hypoxic conditions. Exponentially growing cells were placed in suspension culture and gassed for 90 min in nitrogen or air prior to addition of drugs. Samples were removed periodically for a survival determination, and the ratios determined from a comparison of the resulting survival curves.

d.) Hypoxic Cytoxicity Ratio: Ratio of equitoxic concentrations of each analog for HA-1 cells attained under hypoxic:aerobic conditions. Treatment conditions as above.

e.) Balb/c female mice 3-5 months of age were used in the LD$_{50}$ experiments. LD$_{50}$ was evaluated as described in Example 18.

As may be readily deduced from the table, novel compounds 14, 18a, and 21 exhibit significantly enhanced cytotoxicity against hypoxic HA-1 tumor cells in vitro compared to 3-amino-1,2,4-benzotriazine 1,4-dioxide (22), while retaining the high differential cytotoxicity against hypoxic cells compared to aerobic cells. These results suggest that these drugs will be more tumor-specific and therefore more effective as antitumor agents in vivo.

EXAMPLE 22

Fractionated Radiotheracy Using 3-Amino-1,2,4-Benzotriazine 1,4-Dioxide

Figure 4:
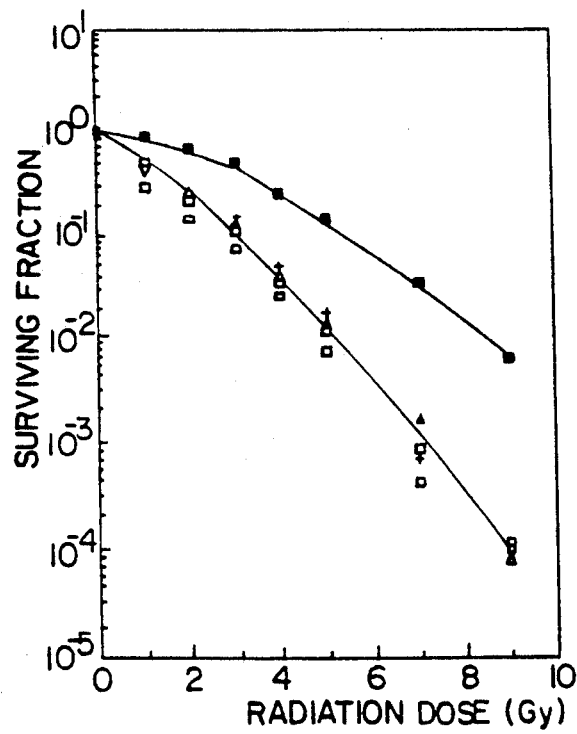
FIG. 4 is a graph illustrating aerobic radiosensitization of CHO cells by hypoxic pretreatment or post-treatment with 3-amino-1,2,4-benzotriazine 1,4-dioxide, as described in Example 22.
Figure 5:
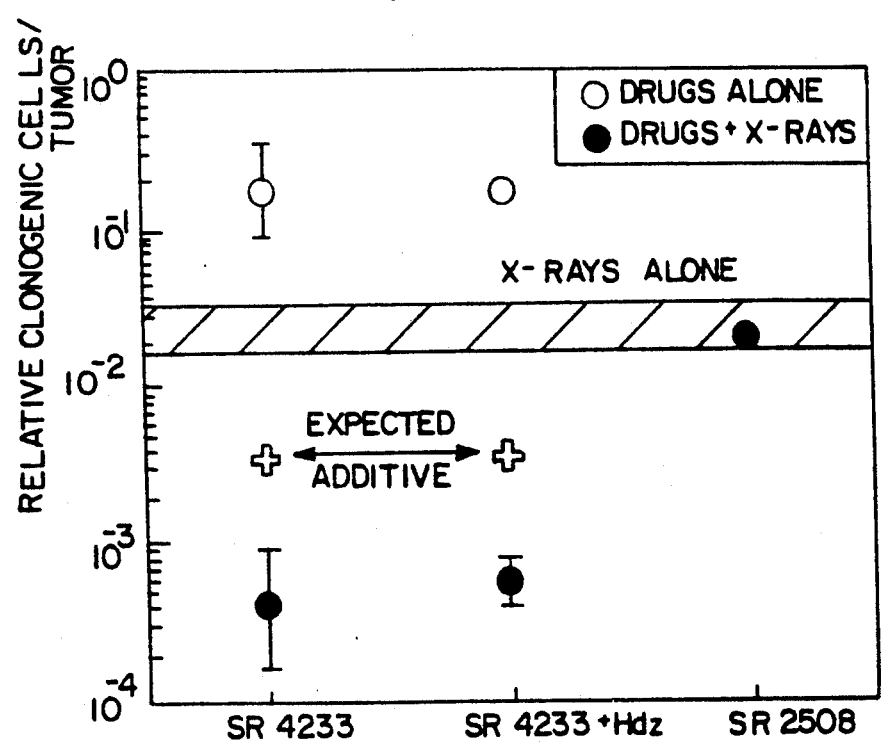
FIG. 5 illustrates tumor cell survival of SCCVII tumor irradiated with 8×2.5 Gy in four days, also as described in Example 22.
Figure 6:
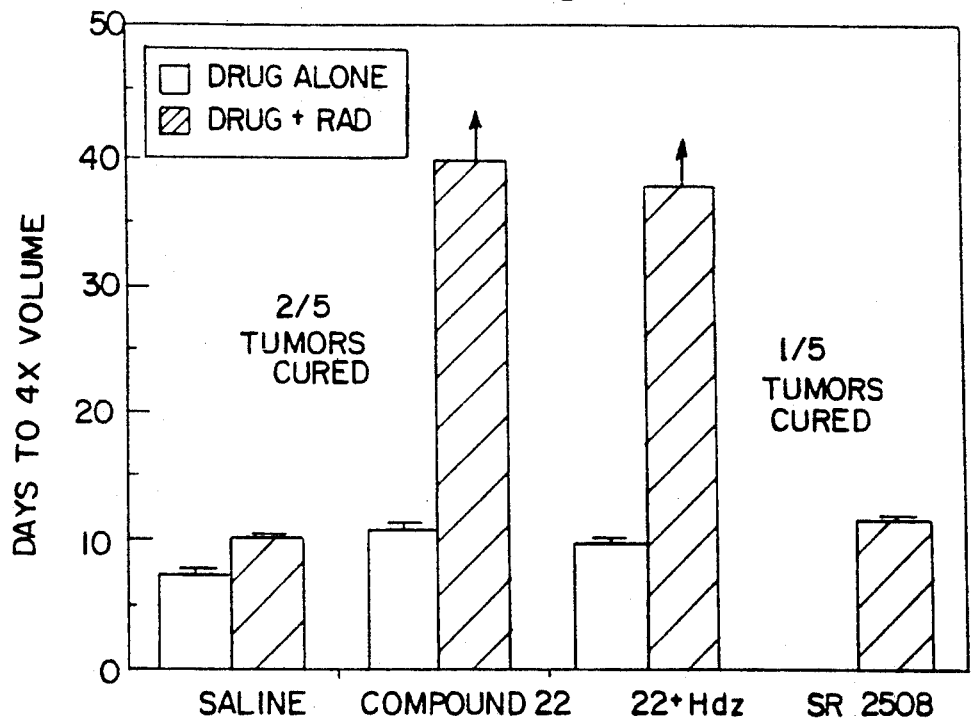
FIG. 6 graphically illustrates the growth delay of SCCVII tumors irradiated with 8×2.5 Gy in four days, also as described in Example 22.

The following experimental work establishes that pre- or post-irradiation treatment of cells in vitro with compound 22 under hypoxic conditions radiosensitizes the cells even when drug is not present during radiation exposure and the cells are aerobic.

a.) FIG. 4 shows the results of experiments in which the survival of Chinese hamster ovary (CHO) cells after graded doses of x-rays was determined either with a hypoxic compound 22 exposure given before or after irradiation. The preirradiation treatments consisted of 20 μM drug for exposure times of 1.0 (□ in FIG. 4), 1.5 (△), 2.0 (◇) and ◙ h. duration prior to cells being reaerated and irradiated. These drug treatments alone reduced cell survival to approximately 32, 19, 8 and 2% respectively. The postirradiation drug treatment consisted of 20 μM for 1.5 h (+), which alone reduced cell survival to 23%. Compared to the survival curve for cells exposed to pre- or post-irradiation hypoxia only (■), treatment with compound 22 sensitized cells to aerobic irradiation. The sensitization was predominantly a change in the slope of the radiation survival curve. $D_o$ decreased from 1.34 Gy (95% confidence limits: 1.09-1.76 Gy) to 0.80 Gy (95% confidence limits: 0.73-0.88 Gy), based on least-squares regression analysis of pooled data for the exponential portions of the survival curves for control and treated cells. However, sensitization at low radiation doses was also readily apparent. Survival ratios for "no drug:drug-treated" CHO cells irradiated with doses of 1-3 Gy averaged a factor of 3.6. The amount of the radiosensitization produced did not vary with the severity of the drug treatment.

b.) The data of section (a.) on radiosensitization of aerobic cells at low radiation doses by hypoxic activation led us to test the feasibility of obtaining preferential radiosensitization of tumors in vivo. Our protocol was to use eight doses of 2.5 Gy/dose in four days (irradiating 2 x/day). Because of the in vitro data showing that radiosensitization could only be achieved by hypoxia activation, either before or after irradiation, and because we did not want to make the tumors hypoxic before irradiation (as this would make them resistant), we made the tumors hypoxic after irradiation using the vasoactive drug hydralazine (HDZ) at the same time as injecting compound 22. We used two different types of controls. First, compound 22 alone before each dose of radiation, and second, the potent hypoxic cell sensitizer SR 2508 (a 2-nitroimidazole, DuPont, undergoing Phase III clinical trials in Europe) before each dose. The effectiveness, or lack of effectiveness, or SR 2508 indicates whether the radiation response of the tumor is being governed by hypoxic, or aerobic, cells respectively. We assayed the efficacies of the treatments using clonogenic cell survival and also regrowth delay. FIGS. 5 and 6 show the results.

As FIG. 5 illustrates, there was no effect of SR 2508 (1000 mg/kg) given before each radiation dose, but compound 22 (0.08 mmole/kg) given alone or with hydralazine (HDZ) produced a large enhancement of the radiation response. Part of this is attributable to an additive response (crosses), but the additional cell killing is the result of radiosensitization of aerobic cells.

In FIG. 6, it may be seen that SR 2508 (1000 mg/kg) before each radiation dose had no radiosensitizing effect, but compound 22 (0.08 mmole/kg) alone before irradiation or with HDZ after irradiation produced a large increase in effect compared to radiation or drug alone.

The major and unexpected result of these experiments is the radiosensitization of the tumors by compound 22 given before each radiation dose without the addition of hydralazine. This cannot be accounted for by a radiosensitization of hypoxic cells, since SR 2508 (a hypoxic radiosensitizer) is ineffective. Thus, it is a radiosensitization of aerobic tumor cells.

Figure 7:
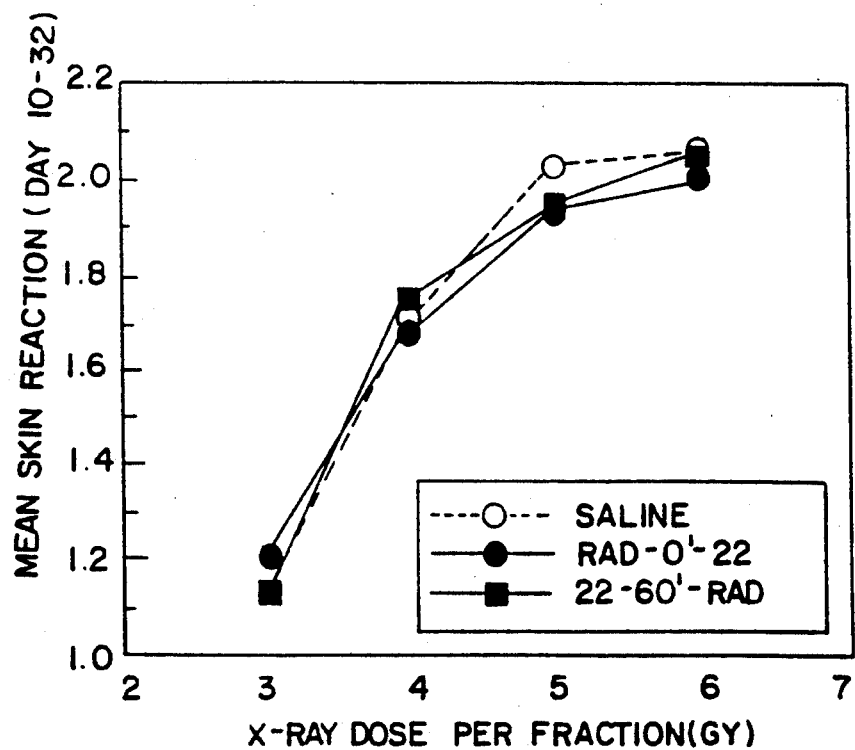
FIG. 7 shows in graph form the average skin reaction of normal mouse skin irradiated with 8 fractions (every 12 hours) of between 3 and 6 Gy per fraction.

This would not be useful if it radiosensitized aerobic normal cells. We tested this by performing the same eight fraction protocol on the response of normal mouse skin using a skin reaction scoring scale previously used by us. FIG. 7 shows the result. There is no radiosensitization of normal skin.

In conclusion, the data show that the aerobic cells of tumors can be radiosensitized in multifraction regimes similar to those used in radiotherapy. The radiosensitization is tumor specific (i.e., does not occur in normal cells), and appears to be the result of activation by hypoxic areas in the tumors.

We claim:

1. A method of synthesizing a 1,2,4-benzotriazine oxide having the structure

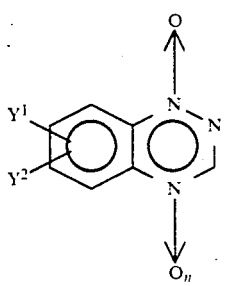

wherein n is 1 and $Y^1$ and $Y^2$ are independently either H; nitro; halogen; hydrocarbyl (1-14C) including cyclic and unsaturated hydrocarbyl; hydrocarbyloxy-hydrocarbyl (1-14C) including cyclic and unsaturated hydrocarbyloxy-hydrocarbyl, if hydrocarbyl or hydrocarbyloxy-hydrocarbyl, either unsubstituted or substituted with 1 or 2 substituents selected from the group consisting of halogen, hydroxy, epoxy, alkoxy (1-4C), alkylthio (1-4C), primary amino ($NH_2$), lower alkyl (1-4C) secondly amino, dialkyl (1-4C) tertiary amino, dialkyl (1-4C) tertiary amino where the two alkyls are linked together to produce a morpholino, pyrrolidino or piperidino ring, $R'COO-$, $R'CONH-$ and thio analogs thereof, acetylaminoalkyl (1-4C), carboxy, alkoxycarbonyl (1-4C), carbamyl, alkylcarbamyl (1-4C), alkylsulfonyl (1-4C) or alkylphosphonyl (1-4C); or wherein $Y^1$ and $Y^2$ are independently either morpholino, pyrrolidino, piperidino, $NH_2$, $NHR'$, $NR'R'$, $O(CO)R$, $NH(CO)R'$, $O(SO)R'$, or $O(POR')R'$, and wherein $R'$ is a hydrocarbyl (1-4C) which may be substituted with one or more OH, $NH_2$, alkyl (1-4C) secondary amino, dialkyl (1-4C) tertiary amino, morpholino, pyrrolidino, piperidino, alkoxy (1-4C), or halogen substituents, or a pharmacologically acceptable salt of said compound, said method comprising:

treating a 3-amino-1,2,4-benzotriazine oxide having the structure

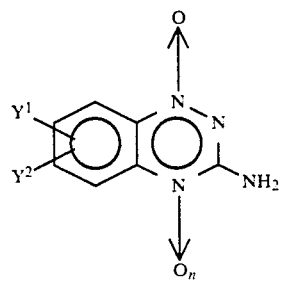

wherein n, $Y^1$ and $Y^2$ are as defined above, with a lower alkyl nitrite under reductive deaminating conditions.

2. The method of claim 1, wherein said lower alkyl nitrite is t-butyl nitrite.

3. The method of claim 1, wherein said reductive deaminating conditions comprise reaction in a compatible solvent at a temperature of at least about 60° C.

4. The method of claim 1, wherein $Y^1$ and $Y^2$ are both H.

5. The method of claim 1, wherein one of $Y^1$ and $Y^2$ is H and the other is nitro.

* * * * *

UNITED STATES PATENT AND TRADEMARK OFFICE
CERTIFICATE OF CORRECTION

PATENT NO. : 5,175,287

DATED : December 29, 1992

INVENTOR(S) : Michael Tracy and Daniel J. Pollart

It is certified that error appears in the above-identified patent and that said Letters Patent is hereby corrected as shown below:

On the title page, in item [75]:
In the names of the inventors, delete "William W. Lee, Palo Alto; J. Martin Brown, Stanford; Edward W. Grange, Palo Alto; Abelardo P. Martinez, San Jose; and delete "all" and substitute therefor -- both --.

Signed and Sealed this

Twenty-first Day of December, 1993

Attest:

BRUCE LEHMAN

Attesting Officer

Commissioner of Patents and Trademarks